(12) United States Patent
Manipatruni et al.

(10) Patent No.: US 9,423,605 B2
(45) Date of Patent: Aug. 23, 2016

(54) OPTOMECHANICAL NON-RECIPROCAL DEVICE

(75) Inventors: Sasikanth Manipatruni, Hillsboro, OR (US); Michal Lipson, Ithaca, NY (US); Jacob T. Robinson, Ithaca, NY (US)

(73) Assignee: Cornell University, Ithaca, NY (US)

( * ) Notice: Subject to any disclaimer, the term of this patent is extended or adjusted under 35 U.S.C. 154(b) by 261 days.

(21) Appl. No.: 13/202,528

(22) PCT Filed: Feb. 19, 2010

(86) PCT No.: PCT/US2010/024806
§ 371 (c)(1),
(2), (4) Date: Oct. 6, 2011

(87) PCT Pub. No.: WO2010/096706
PCT Pub. Date: Aug. 26, 2010

(65) Prior Publication Data
US 2012/0281286 A1 Nov. 8, 2012

Related U.S. Application Data

(60) Provisional application No. 61/153,913, filed on Feb. 19, 2009.

(51) Int. Cl.
*G02B 26/00* (2006.01)
*G02B 6/42* (2006.01)
(Continued)

(52) U.S. Cl.
CPC ............ *G02B 26/001* (2013.01); *G02B 6/4209* (2013.01); *A61F 9/022* (2013.01); *B81B 2201/04* (2013.01); *G02B 1/005* (2013.01); *H01S 3/005* (2013.01)

(58) Field of Classification Search
USPC .......... 359/198.1–199.4, 200.6–200.8, 202.1, 359/221.2, 223.1–225.1, 226.2, 904, 359/290–295, 838, 846, 871, 872, 237, 238, 359/577, 578, 580, 583, 584, 586, 588, 589, 359/582; 250/204, 559.06, 559.29, 230, 250/234; 347/255–260; 353/39, 98–99; 385/15–18, 22; 398/12, 19, 45; 356/450–455, 477–480, 482–483, 519
See application file for complete search history.

(56) References Cited

U.S. PATENT DOCUMENTS 6,580,516 B1 * 6/2003 Tucker et al. ................ 356/519
6,714,565 B1 * 3/2004 Tucker et al. .................. 372/20
(Continued)

FOREIGN PATENT DOCUMENTS

GB 2320105 10/1998
WO WO 2009/125014 A2 10/2009

OTHER PUBLICATIONS

Patent Cooperation Treaty, International Search Report and Written Opinion, International Application Number: PCT/US2010/024806, dated Sep. 13, 2010 (9 pages).
(Continued)

*Primary Examiner* — Stephone B Allen
*Assistant Examiner* — James McGee
(74) *Attorney, Agent, or Firm* — Heslin Rothenberg Farley & Mesiti P.C.

(57) ABSTRACT

There is set forth herein an optomechanical device which can comprise a first mirror and a second mirror forming with the first mirror a cavity. In one aspect the first mirror can be a movable mirror. The optomechanical device can be adapted so that the first mirror is moveable responsively to radiation force.

40 Claims, 21 Drawing Sheets

(51) Int. Cl.
*A61F 9/02* (2006.01)
*G02B 1/00* (2006.01)
*H01S 3/00* (2006.01)

(56) References Cited

U.S. PATENT DOCUMENTS

| | | | |
|---|---|---|---|
| 7,450,295 B2 * | 11/2008 | Tung et al. | 359/290 |
| 7,583,874 B2 | 9/2009 | Rakich et al. | |
| 8,174,698 B2 * | 5/2012 | Peter et al. | 356/432 |
| 2007/0097694 A1 * | 5/2007 | Faase et al. | 362/319 |
| 2009/0153844 A1 | 6/2009 | Peter et al. | |

OTHER PUBLICATIONS

Kippenberg, T.J. et al. "Analysis of Radiation-Pressure Induced Mechanical Oscillation of an Optical Microcavity," The American Physical Society, dated Jul. 15, 2005 (4 pages).

Manipatruni, Sasikanth et al. "Optical Nonreciprocity in Optomechanical Structures," The American Physical Society, dated May 29, 2009 (4 pages).

* cited by examiner

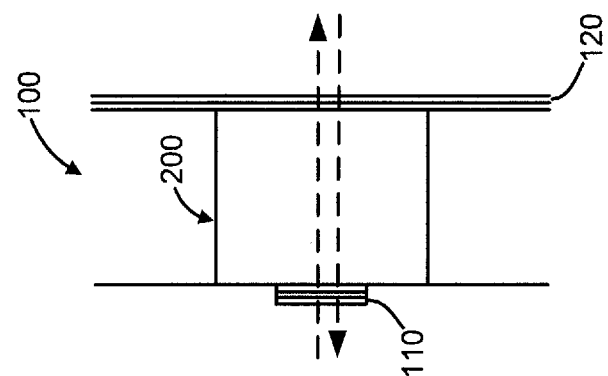
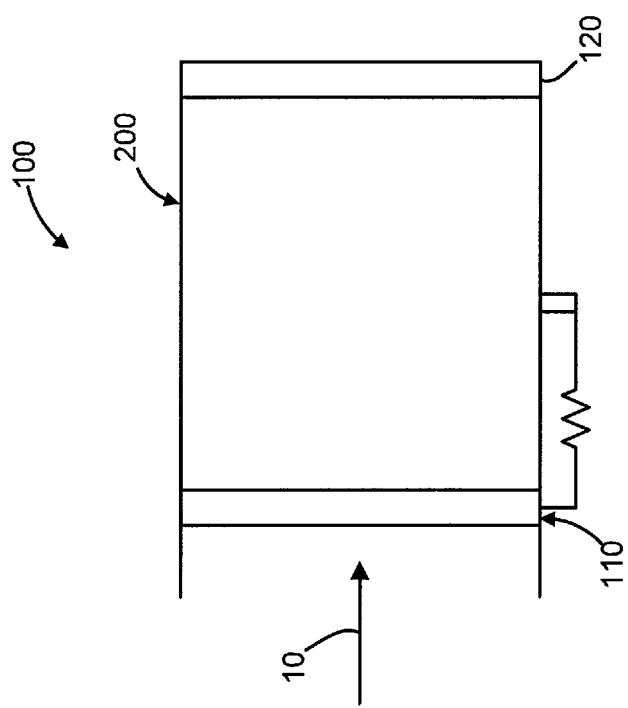

LOW POWER PASS
INITIAL STATE:
CAVITY RESONANCE BAND MATCHED TO
CENTRAL WAVELENGTH OF INCIDENT LIGHT

HIGH POWER PASS
INITIAL STATE:
CAVITY RESONANCE BAND NOT MATCHED TO
CENTRAL WAVELENGTH OF INCIDENT LIGHT

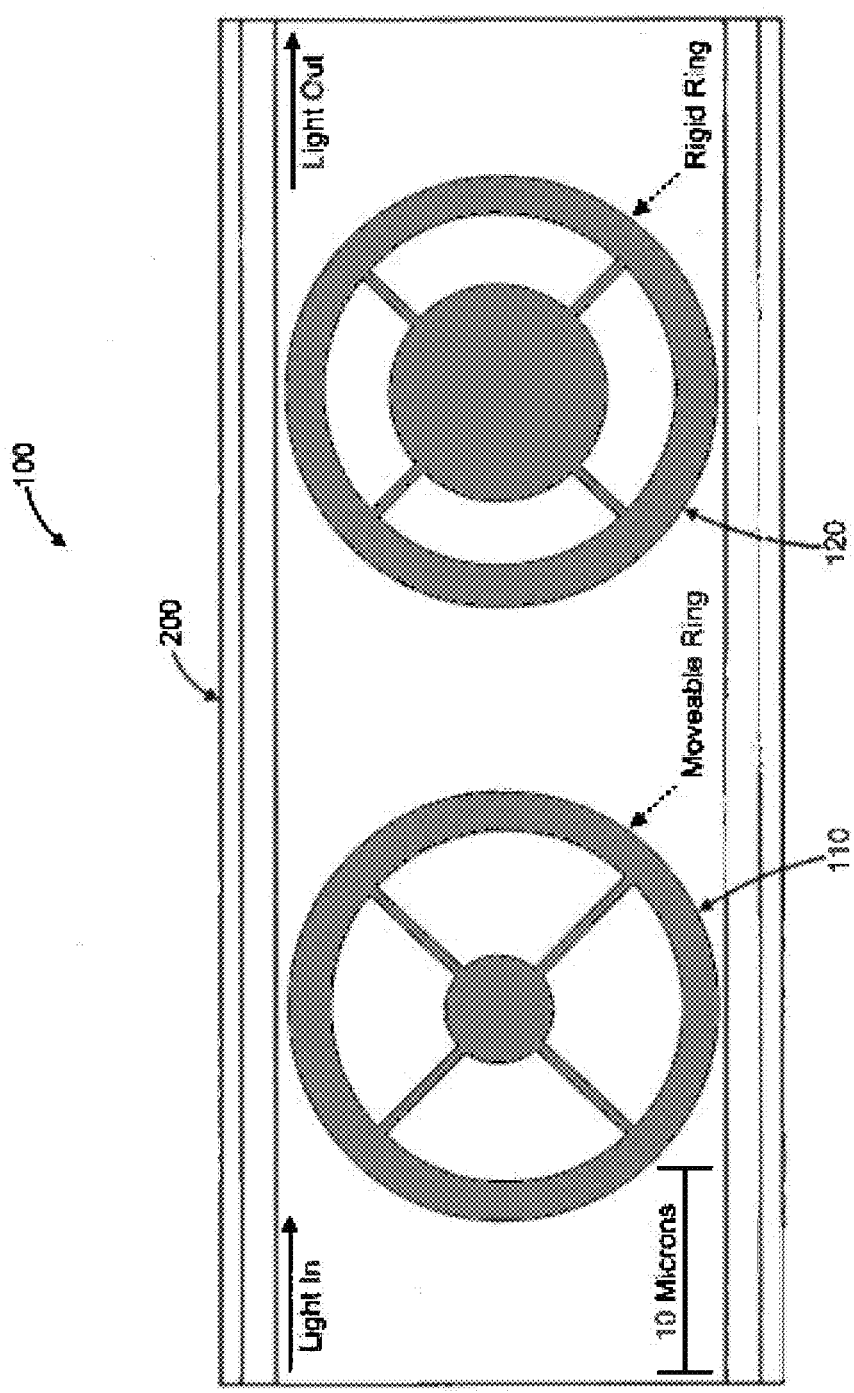

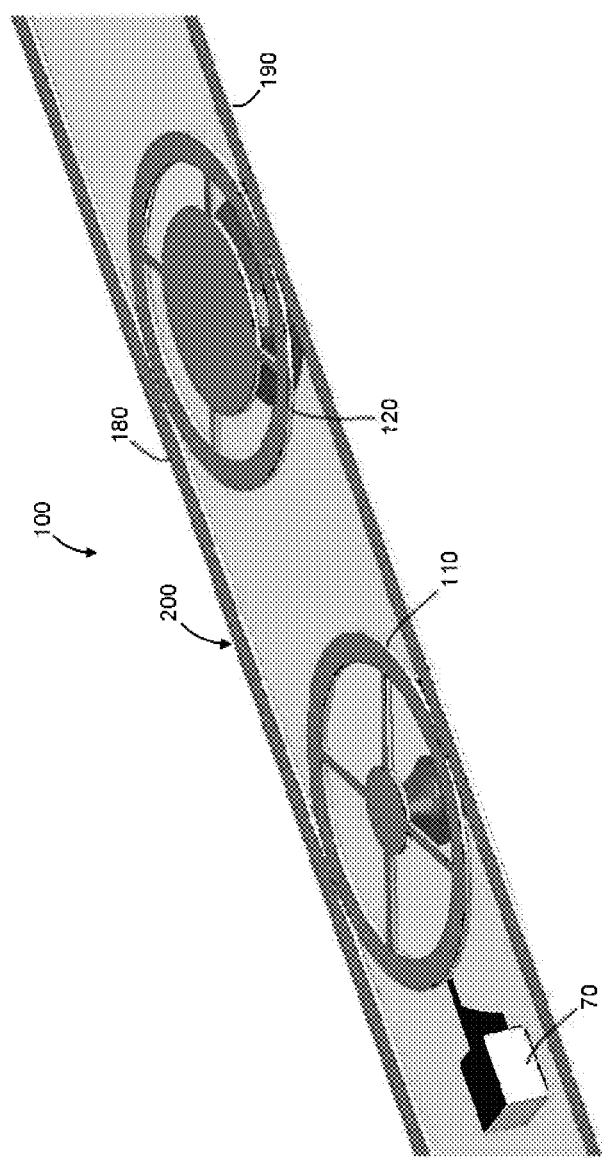

OPTOMECHANICAL NON-RECIPROCAL DEVICE

CROSS REFERENCE TO RELATED APPLICATIONS

This application is a National Stage application under 35 U.S.C. §371 of PCT Application No. PCT/US2010/024806, filed Feb. 19, 2010, entitled "Optomechanical Non-Reciprocal Device," which claims priority to U.S. Application No. 61/153,913, filed Feb. 19, 2009, entitled "Optomechanical Non-Reciprocal Device,"," which is incorporated herein by reference.

FIELD OF THE INVENTION

This invention relates generally to optomechanical devices, and more specifically to optomechanical devices capable of exhibiting non-reciprocal behavior.

BACKGROUND OF THE INVENTION

Recent work in optomechanics, enabled by advances in optical micro cavities and nano-electro-mechanical systems, has shown tremendous potential for new classes of micro scale devices and phenomena.

Traditional methods for providing non reciprocal devices rely on magneto-optic media, optically active media, or electro-optic crystals. According to a non-reciprocal optical system based on magneto-optical gyrotropy, a forward propagating right circularly polarized mode can be transformed by the operation of time reversal to a backward propagating mode that is also right circularly polarized. In a non-reciprocal optical system based on electro-optic crystals, non-reciprocity can take the form of two-wave mixing and can incorporate a phase grating that can be displaced from a fringe pattern generated by two waves being mixed.

SUMMARY OF THE INVENTION

There is set forth herein an optomechanical device which can comprise a first mirror and a second mirror forming with the first mirror a cavity. In one aspect the first mirror can be a movable mirror. The optomechanical device can be adapted so that the first mirror is moveable responsively to radiation force.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIG. 1 is a side schematic view of an optomechanical device having an optical cavity.

FIG. 2 is a side view illustrating fabrication detail for the optomechanical device of FIG. 1.

FIG. 15 is a top view of an in-line non-reciprocal optomechanical device.

FIG. 16 is a perspective view of the optomechanical device of FIG. 15.

DETAILED DESCRIPTION OF THE INVENTION

Figure 3:
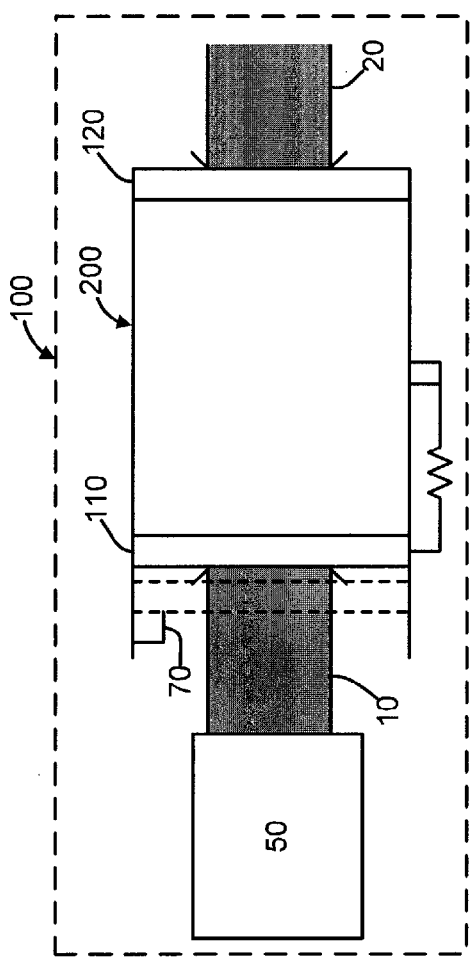
FIG. 3 is a side schematic view of an optomechanical device operative as an isolator.

There is set forth herein an optomechanical device 100 which can comprise a first mirror 110 and a second mirror 120 forming with the first mirror a cavity 200. In one aspect the first mirror 110 can be a movable mirror.

Optomechanical device 100 can be adapted so that first mirror 110 is moveable responsively to radiation forces resulting from the emission of light. Radiation force can also be expressed as "radiation pressure," force per unit area. In the development of optomechanical device 100 it was determined that if a mass of first mirror 110 is sufficiently small, (e.g., nanoscale) and is appropriately arranged, mirror 110 can moved by radiation force resulting from incident light incident from a commercially available light source. In one embodiment, a light source can be operatively disposed in an optomechanical device including a light source and a cavity. In one embodiment, an optomechanical device can be operatively disposed to interact with light from an unknown light source.

The force imparted by light beam 10 can be given by $$F = P/c \quad [\text{Eq. 1}]$$

Where P is the power of the beam, and c is the speed of light in a vacuum. Accordingly, for a light beam emitted by a commercially available light source, the beam can be expected to impart a force on a mechanical object of on order of nN (nanonewtons), which for many applications can be ignored. In embodiments set forth herein, movable mirror 110 can be provided in such form (e.g., as a nanoscale apparatus) and can be appropriately arranged as to be movable by radiation forces resulting from emission of light from a commercially available light source. In one embodiment, a sum of forces (net force) on a movable mirror of an optical cavity can include a sum of an incident radiation force, a reflective radiation force, and a cavity buildup radiation force.

An aspect of cavity 200 as shown in the embodiment of FIG. 1 is that a transmittivity (transmission) wavelength band (resonance wavelength band) of cavity 200 is dependant on a relative distance spacing of first mirror 110 and second mirror 120. A position dependent reflectively $R(\lambda, x, t)$ of a cavity as shown in FIG. 1 as a function of a displacement, x of, mirror 110 can be given by:

$$R(\lambda, x, t) = 1 - \left[ \left( \frac{|t_1 t_2|}{1 - |r_1 r_2|} \right)^2 \frac{1}{1 + 4\left( \frac{\sqrt{|r_1 r_2|}}{1 - |r_1 r_2|} \right)^2 \sin^2 \varphi(x)} \right]^{1/2} \quad [\text{Eq. 2}]$$

where $\varphi(x)$ is the phase shift per round trip inside the cavity:

$$\frac{1}{2} \text{Arg}\left[ r_1 r_2 e^{i\frac{2\pi}{\lambda}(l-x)} \right]$$

and $r_1$, $r_2$ & $t_1$, $t_2$ are the mirror reflectivities and transmittivities; $l$ is the steady state cavity length.

Accordingly, if input light energy results in a change in relative spacing of the first mirror 110 and the second mirror 120, a shift in the resonance wavelength band of cavity 200 can be expected. In optomechanical devices set forth herein various arrangements of cavities including a movable mirror responsive to radiation force are provided. In some embodiments described herein, an optomechanical device can include an associated light source which has an emission band and/or power emission characteristics that are complementarily selected with characteristics of cavity 200.

In another aspect, a moveable mirror 110 of cavity 200 can be made moveable by way of a number of alternative mounting structures. Mounting structures for making a mirror of device 110 movable include cantilevers. Alternate methods of mechanical suspension can be selected including electrical, optical, magnetic levitation, microfluidic. Mirrors 110, 120 in one embodiment can be provided, e.g., by distributed Bragg gratings having layers of alternating diffractive indices, photonic crystals, and in-plane mirrors.

A diagram illustrating an exemplary construction of optomechanical device 100 is shown in FIG. 2. Optomechanical device 100 can be formed using a solid state material platform. In one embodiment, fabrication of optomechanical device 100 can include straight forward lithography, etching, and deposit steps. A material stack of silicon and oxide can be etched from an oxide side. Poly-silicon and oxide can be deposited to form Bragg reflectors with appropriate thicknesses. Mirrors 110, 120 forming cavity 200 can be formed in a high index of refraction system (e.g., refractive index of silicon 3.5, refractive index of oxide (1.5)) using a quarter wave stack. A mechanical suspension for first mirror 110 can be provided by a system of silicon cantilevers.

In one embodiment, cavity 200 can exhibit characteristics that are non-reciprocal, i.e., cavity 200 can be operative to interact with incident light incident in a first direction differently from light that is incident in a second direction. In cavity 200, first mirror 110 can be provided by a movable mirror and second mirror 120 can be a stationary mirror. For a light beam incident on cavity 200 in a first direction (incident first on the first mirror 110) at the optical resonance wavelength (frequency), the net momentum imparted per second on the movable mirror is $-((2\eta-1)-R)I/c$ (where $\eta$ is the power build up factor of the cavity, R is the power reflectivity of the FP cavity, I is the incident power and c is the speed of light in vacuum, and the negative sign indicates that the direction of the force is away from the cavity). For a light beam incident on cavity 200 in a second direction (incident first on second mirror 120 which is stationary in the example) the net momentum imparted per second on the movable mirror is $-((2\eta-1)+R)\backslash1c$. Hence the differential radiation force for left and right incident beams is 2RIZc producing a non-reciprocal mechanical response from first mirror 110 leading to non-reciprocal optical transmittivity (transmission) spectra. There is set forth herein a method comprising providing an optomechanical device, the optomechanical device being adapted so that forward incident light results in a first set of radiation forces being imparted to optomechanical device, the optomechanical device further being adapted so that backward incident light results in a second set of radiation forces being imparted to the optomechanical device, the optomechanical device having a first transmittivity band when the first set of forces are imparted to the optomechanical device, the optomechanical device having a second transmittivity band when the second set of forces are imparted to the optomechanical device; and directing light toward the optomechanical device at a central wavelength matching the first transmittivity band.

A diagram illustrating an optical transmittivity (transmission) spectra of optomechanical device 110 in one embodiment is shown in FIG. 3. It is seen that because of the non-reciprocal mechanical response of cavity 200, a transmittance bandwidth of a forward incident light beam incident on the cavity in a first direction can be differentiated from a backward incident light beam incident on the cavity in a second direction.

An exemplary practical application for optomechanical device 100 which exhibits non-reciprocal behavior is shown and described in relation in FIG. 3. In the embodiment of FIG. 3, optomechanical device 100 includes an associated light source 50. Light source 50 can be operative to emit coherent light at a certain central wavelength. Light source 50 in one embodiment can be a laser light source. A risk to the operation of light source 50 is posed by reflected returned light having the certain central wavelength that can be reflected from an object external to light source and reflected back to light source 50. In the embodiment of FIG. 3, cavity 200 is operative as an optical isolator to isolate reflected returned light and to prevent returned reflected light from being transmitted to light source 50. Referring to the plot of FIG. 4, it is seen that reflected light at the certain central wavelength of light emitted from light source 50 incident on cavity 200 and within the transmittivity band of cavity 200 in the forward direction can be reflected or absorbed by cavity 200 rather than transmitted.

Figure 4:
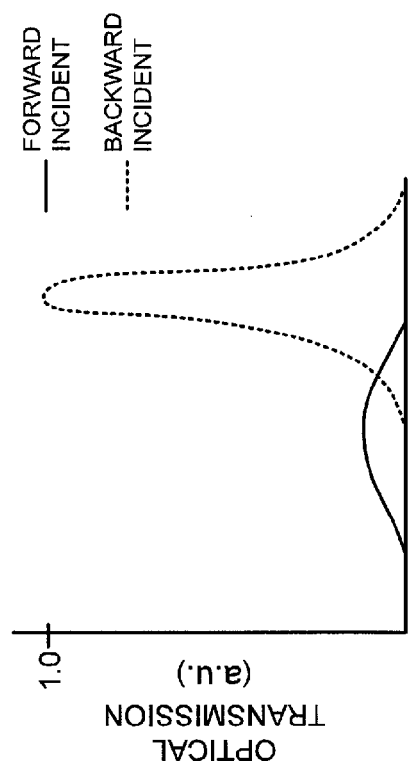
FIG. 4 is a transmittance plot for the optomechanical device as shown in FIG. 3.

In the embodiment of FIG. 4, peak transmittivity in the forward direction is approximately 0.1 of the transmittivity (of about 1.0) in the backward direction. It will be seen that where a forward incident beam is in the direction of backward beam 20, the forward incident beam would have a peak transmittivity of about unity (about 1.0), with backward incident beam having a transmittivity of about 0.1. As has been described, the sum of forces (net force) incident on mirror 110 in the forward direction will be unequal to the net force incident on mirror 110 in the backward direction. Accordingly, it will be seen that the net force incident on mirror 110 will be unequal in the case that forward and backward light are simultaneously incident on cavity 200. The case where forward and backward light are simultaneously incident on cavity 200 occurs where a forward incident light beam is active at the time reflected light is received. Because the net force on mirror 110 in case of simultaneously incident forward and backward light is not equal to the net force incident or mirror 110 when only a forward beam is incident on cavity, there will be a shift in the resonance wavelength band of cavity 200 where reflected light is received by cavity 200 with a forward incident beam simultaneously active. In one embodiment, cavity 200 can be configured so that cavity 200 is in resonance on the condition that forward propagating light only is incident therein but not in resonance (and not transmitting) in the case of forward and backward light being simultaneously incident (as in the case of reflection with a forward incident beam active). The "not transmit" condition herein in one embodiment can be regarded as the condition at which transmittivity is below a predetermined low threshold.

Accordingly, cavity 200 can be configured to exhibit non-transmittive characteristics when forward and backward light are simultaneously incident, and/or when backward light only is incident on cavity 200. In one embodiment, device 100 can be configured so that light source 50 emits pulsed light with continuously switching on and off states, wherein reflection can be expected to be received during the off states. In such embodiment, cavity 200 can be configured to perform an isolation function by being configured to exhibit non-transmittive characteristics when backward light only is incident thereon. There is set forth herein an optomechanical device comprising a light source; a first mirror; and a second mirror forming with the first mirror a cavity; wherein the first mirror is a movable mirror; wherein the optomechanical device is adapted so that the first mirror is moveable responsively to radiation force; wherein the light source emits light at a certain central wavelength, and wherein the optomechanical device is operative so that light emitted from the light source incident on the cavity in a forward direction results in a first set of radiation forces being imparted on the first mirror, and wherein the optomechanical device is further operative so that reflected light having the certain central wavelength incident on the cavity in a backward direction simultaneously with light from the light source being incident on the cavity in the forward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction simultaneously with light from the light source being incident on the cavity in the forward direction, wherein the certain central wavelength is matched to the first resonance wavelength band but not matched to the second resonance wavelength band so that the reflected light at the certain central wavelength is not transmitted by the cavity.

By movement of a distance spacing of first mirror 110 relative to second mirror 120, a resonance band of cavity 200 can be shifted. A plot indicating a peak transmission wavelength as a function of distance spacing is shown at FIG. 4. In the development of optomechanical device 100 it was determined that maintaining a distance spacing of first mirror 110, which can be moveable at a certain spacing distance may be challenging in view of practical imperfections of a light source, first mirror 110 and the mechanical suspension for arranging first mirror 110, and further in view of characteristics of the various elements of cavity 200 under resonance.

Accordingly, in view of an expected instability of moveable mirror 110, an optomechanical device as set forth herein can in include a mechanical stop 70 for stopping movement of the mirror in one direction in response to an imparted radiation force. Features of a mechanical stop in one embodiment are as follows. In one aspect, a mechanical stop 70 can have a spring constant sufficient so that movement of mirror 110 is restricted to provide stable positioning of mirror 110. In another aspect, a mechanical stop 70 can be provided so as to be resistant to adhering with externally disposed objects such as mirror 110. For example, stop 70 can be provided to have a polymer coating, or can be fabricated using special fabrication methods. Further, a mechanical stop 70 can be configured to provide a damped response, e.g., with minimal or without oscillations. Still further, stop 70 should be arranged to they are not to affect an optical function of a cavity.

A mechanical stop 70 can be provided for limiting a maximum distance at which a first and second mirror 110, 120 can be spaced.

Figure 5:
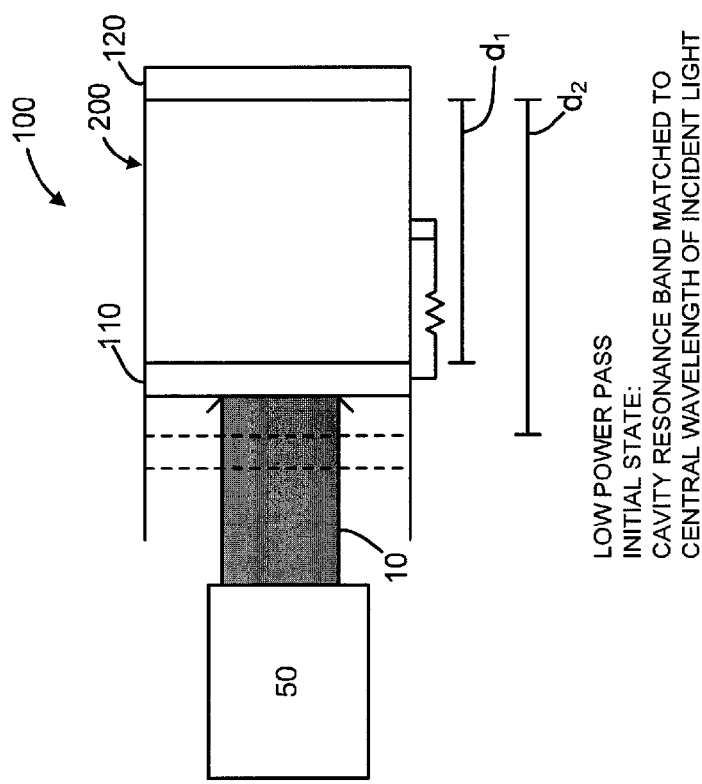
FIG. 5 is a side schematic view of an optomechanical device operative to selectively pass light at low power.

In the embodiment of FIG. 5, optomechanical device 100 can be provided to limit a power of light transmitted by a light source. In the embodiment of FIG. 5, light source 50 can be disposed to project light onto cavity 200, and cavity 200 can be arranged to limit light transmitted at higher powers. Optomechanical device 100 in the embodiment of FIG. 5 can be regarded as a power limiter.

Figure 6:
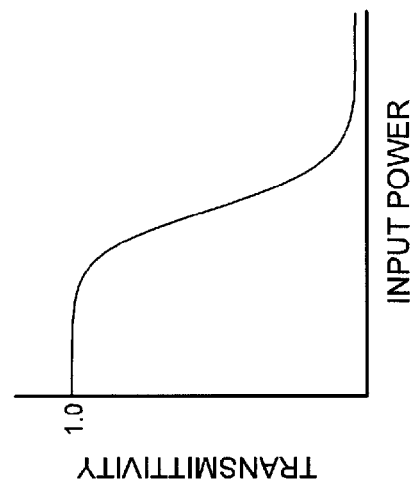
FIG. 6 is a transmittance plot for the optomechanical device as shown in FIG. 5.

Cavity 200 can be provided so that in an initial state cavity 200 has a resonance wavelength band that is matched to the emission central wavelength. However, cavity 200 can also be adapted so that on receipt by cavity 200 of incident light, mirror 110 can move to shift a resonance wavelength band of cavity 200. It will be seen that the amount of the shift can be a function of the power of the incident light. A plot showing cavity transmittivity as a function of input light energy is shown in FIG. 6. It is seen that as the power of the emitted light increases moving mirror 110 can move to shift a resonance wavelength of cavity 200. At some point in the shift a resonance band of the cavity 200 can be expected to become mismatched relative to the central wavelength of the incident light incident on cavity 200. At such point cavity 200 will not transmit. As indicated, the "not transmit" condition herein in one embodiment can be regarded as the condition at which a transmittivity is below predetermined low threshold. Referring to the power limiter example of FIG. 5, it can be seen that when sufficiently high power light is incident on cavity 200, a resonance wavelength band of cavity 200 can shift between a first resonance wavelength band matched to a certain central wavelength to a second resonance wavelength band not matched to a certain central wavelength. There is set forth herein an optomechanical device comprising a first mirror; and a second mirror forming with the first mirror a cavity; wherein the first mirror is a movable mirror; wherein the optomechanical device is adapted so that the first mirror is moveable responsively to radiation force; wherein during an initial state a resonance wavelength band of the cavity is matched to a certain central wavelength so that the cavity is capable of transmitting light emitted from a light source that emits light at the certain central wavelength, and wherein the optomechanical device is adapted so that a set of radiation forces on the first mirror attributable to emission of light at the certain central wavelength with sufficient power results in a resonance wavelength band of the cavity shifting from a wavelength band at which the resonance wavelength band of the cavity is matched to the certain central wavelength to a wavelength band at which the resonance wavelength band is not matched to the certain central wavelength.

A summary of states of the optomechanical device of FIG. 5 is summarized in Table A below.

TABLE A

| State | Power of Emitted Light | Mirror Spacing | Resonance of Cavity | Result |
|---|---|---|---|---|
| Initial | No Power | $d_1$ | Not Matched to Central Wavelength of Incident Beam | No Initial Beam |
| Low Power | Low Power | $d_1$ | Matched to Central Wavelength of Incident Beam | Beam is Transmitted |
| High Power | High Power | $d_2$ | Not Matched to Central Wavelength of Incident Beam | Beam is Not Transmitted |

Figure 8:
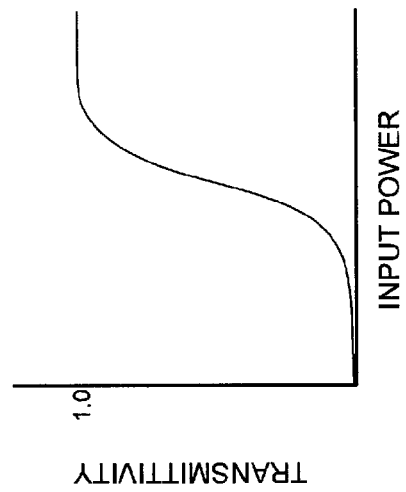
FIG. 8 is a transmittance plot for the optomechanical device as shown in FIG. 6.
Figure 7:
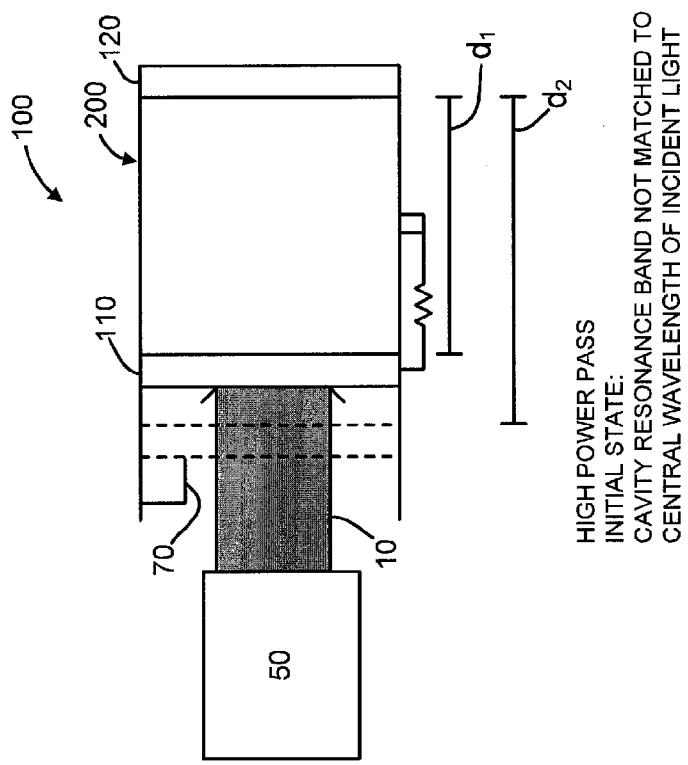
FIG. 7 is a side schematic view of an optomechanical device operative to selectively transmit light at high power.

In the embodiment of FIG. 7, optomechanical device 100 can be provide to restrict transmittance of low power incident light, and selectively transmit light at higher powers. In the embodiment of FIG. 7, light source 50 is disposed to project light onto cavity 200, and cavity 200 is arranged to limit light transmitted at lower powers. Referring to FIG. 7, light source 50 can emit light at a certain central wavelength and can be a variable power light source variable to emit light having wattage of between 0W and NW. Cavity 200 can be provided so that in an initial state cavity 200 has a resonance wavelength band that matches the emission central wavelength. However, cavity 200 can also be adapted so that on receipt of incident light, mirror 110 can move to shift a resonance wavelength band of cavity 200. It will be seen that the amount of the shift can be a function of the power of the incident light. A plot showing cavity transmittivity as a function of input light energy is shown in FIG. 8. It is seen that as the power of the emitted light increases moving mirror 110 can move to shift a resonance wavelength of cavity 200. At some point in the shift, a resonance band of the cavity 200 can be expected to become matched relative to the central wavelength of the incident light. At such point cavity 200 is capable of transmitting. In the embodiment of FIG. 7, optomechanical device 100 can include stop 70 for aiding the stabilizing of mirror 110 at a certain position to yield a stable resonance frequency band for cavity 200. An optomechanical device 100 as set forth in FIG. 7 can be regarded as a saturable absorber. A saturable absorber as described with reference to FIG. 7 can be utilized in combination with a laser light source for mode locking. Referring to the embodiment of FIG. 7, it can be seen that where sufficiently high power light is incident on cavity 200, a resonant wavelength band of cavity 200 can shift between a first resonant wavelength band not matched to a central wavelength of emitted light to a second resonant wavelength band matched to a central wavelength of emitted light. There is set forth herein an optomechanical device comprising a first mirror; and a second mirror forming with the first mirror a cavity; wherein the first mirror is a movable mirror; wherein the optomechanical device is adapted so that the first mirror is moveable responsively to radiation force; wherein during an initial state a resonance wavelength band of the cavity is not matched to a certain central wavelength so that in an initial state the cavity is restricted from transmitting light emitted from a light source at the certain central wavelength, and wherein the optomechanical device is adapted so that a set of radiation forces on the first mirror attributable to emission of light at the certain central wavelength with sufficient power results in a resonance wavelength band of the cavity shifting from a wavelength band at which the resonance wavelength band of the cavity is not matched to the certain central wavelength to a wavelength band at which the resonance wavelength band of the cavity is matched to the certain central wavelength.

Table B summarizes possible states of the optomechanical device of FIG. 7.

TABLE B

| State | Power of Emitted Light | Mirror Spacing | Resonance of Cavity | Result |
|---|---|---|---|---|
| Initial | No Power | $d_1$ | Matched to Central Wavelength of Incident Beam | No Initial Beam |
| Low Power | Low Power | $d_1$ | Not Matched to Central Wavelength of Incident Beam | Beam is Not Transmitted |
| High Power | High Power | $d_2$ | Matched to Central Wavelength of Incident Beam | Beam is Transmitted |

Figure 10:
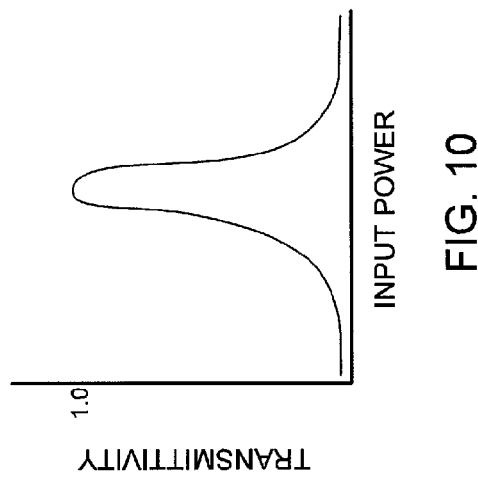
FIG. 10 is a transmittance plot for the optomechanical device as shown in FIG. 9.
Figure 9:
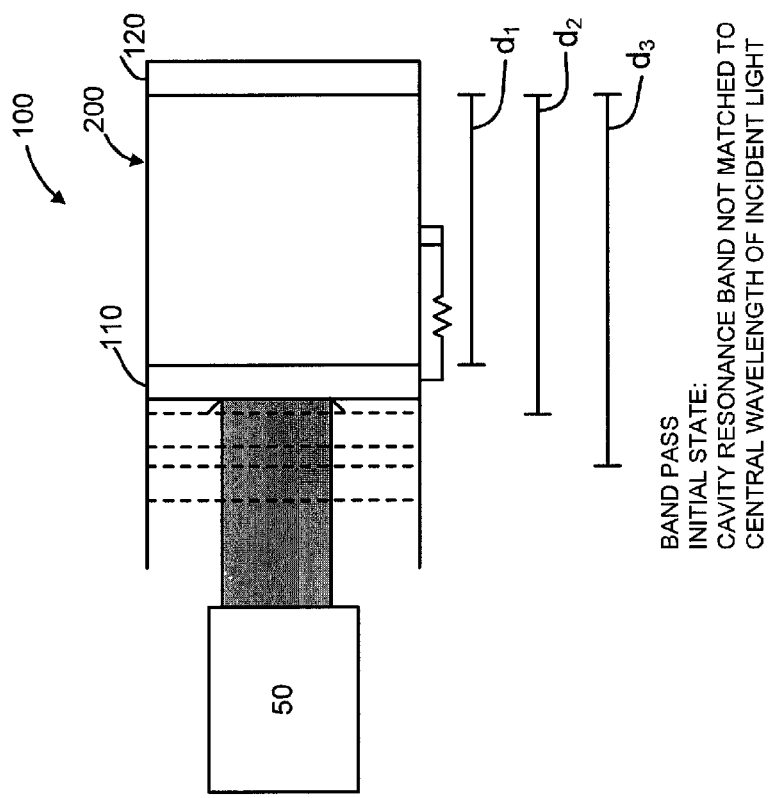
FIG. 9 is a side schematic view of an optomechanical device operative to selectively transmit light at intermediate power.

In the embodiment of FIG. 9, optomechanical device 100 is operative to provide a power band pass function; that is, transmit light emitted within a predetermined power band for a particular central wavelength of emission, but not transmit light emitted at power either less than or greater than the power pass band. A transmittivity plot for the device of FIG. 9 is shown in FIG. 10. In an initial state, cavity 200 is in a state where it does not transmit light incident at the central wavelength of the incident light. At intermediate power, a resonance band can become matched with the central wavelength of the incident light and cavity 200 can transmit emitted light emitted from light source 50. At higher power, a distance between mirror 110, 120 can change again to change a resonance band of cavity 200 again so that cavity 200 again becomes mismatched with the resonance band of the incident light so that cavity 200 again does not transmit. Referring to the example of FIG. 9, it can be seen that when appropriately high power light is incident on the cavity of FIG. 9 at a certain central wavelength, a resonance wavelength band can shift between a first resonance wavelength band at which the resonance wavelength band is not matched to a central wavelength, a second resonance wavelength band at which the resonance wavelength band is matched to a central wavelength, and a third resonance wavelength band at which the resonance wavelength band is not matched to a central wavelength. There is set forth herein an optomechanical device comprising a first mirror; and a second mirror forming with the first mirror a cavity; wherein the first mirror is a movable mirror; wherein the optomechanical device is adapted so that radiation force on the first mirror attributable to emission of light of a certain central wavelength with sufficient power results in a resonance wavelength band of the cavity shifting between a first state in which a resonance wavelength band of the cavity includes a set of wavelengths shorter than a wavelength band matched to a certain central wavelength, a second state in which a resonance wavelength band of the emitted light is matched to a the certain central wavelength, and the third state in which the resonance wavelength band of the cavity includes a set of wavelengths longer than a wavelength band matched to the certain central wavelength. A summary of states of the embodiment of FIG. 9 is summarized in Table C.

TABLE C

Table C

| State | Power of Emitted Light | Mirror Spacing | Resonance of Cavity | Result |
| --- | --- | --- | --- | --- |
| Initial | No Power | $d_1$ | Not Matched to Central Wavelength of Incident Beam | No Initial Beam |
| Low Power | Low Power | $d_1$ | Not Matched to Central Wavelength of Incident Beam | Beam is Not Transmitted |
| Intermediate Power | Intermediate Power | $d_2$ | Matched to Central Wavelength of Incident Beam | Beam is Transmitted |
| High Power | High Power | $d_3$ | Not Matched to Central Wavelength of Incident Beam | Beam is Not Transmitted |

Figure 11:
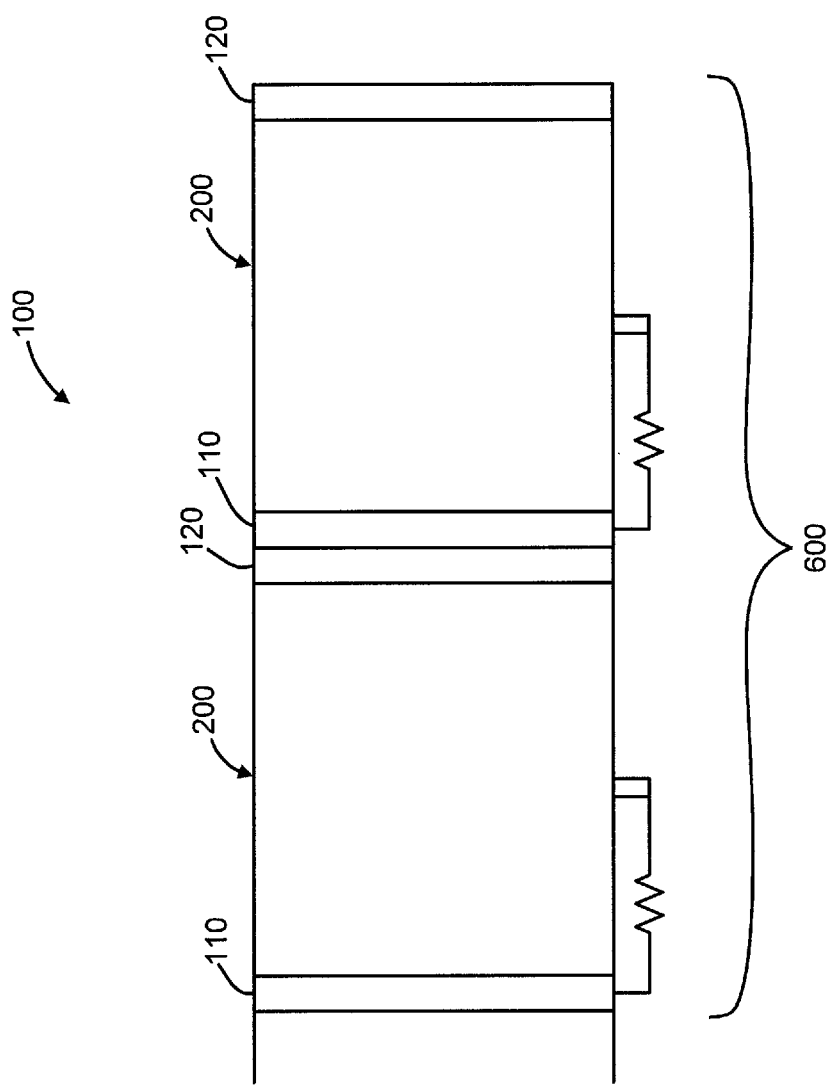
FIG. 11 is a perspective schematic view of an optomechanical device including a plurality of optical cavities arranged in series.
Figure 12:
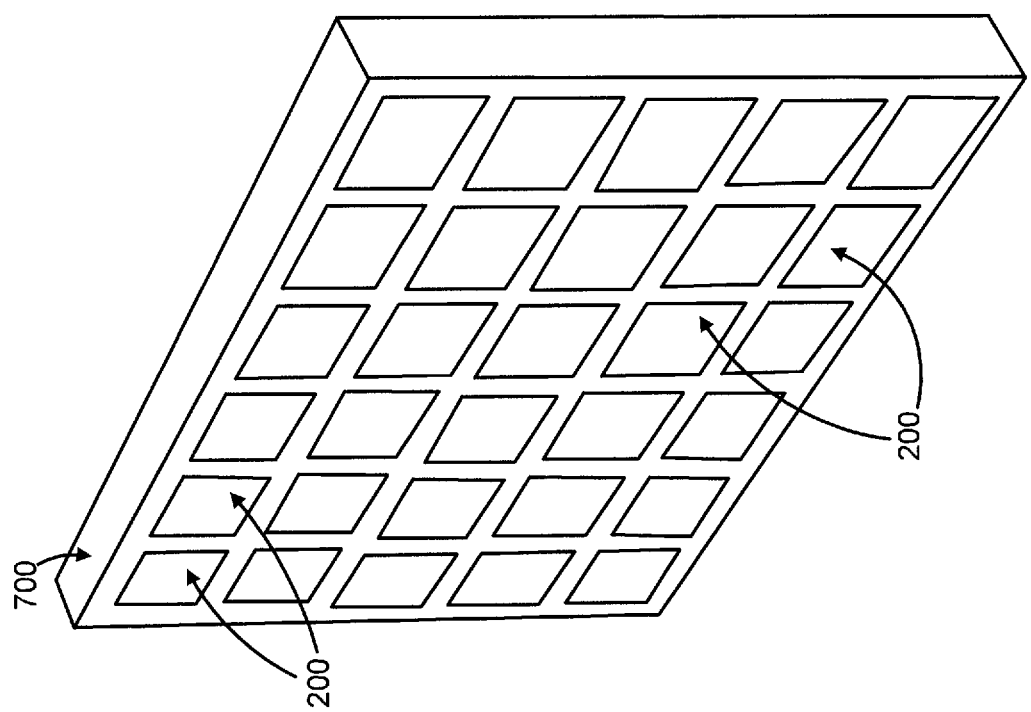
FIG. 12 is a perspective schematic view of an optomechanical device including a two dimensional array of optical cavities.

For scaling up optical systems in which a cavity 200 as described are incorporated, cavity 200 can be incorporated into arrays of cavities. In FIG. 11, there is shown an array 600 of cavities 200 formed in a one dimensional array of cavities 200 in which cavities 200 are arranged in series so that axes of adjacent ones of cavities 200 are aligned. Such arrangement can be useful for achieving complex transmittivity characteristics for optomechanical device 100. In FIG. 12, there is shown an array of cavities formed as a two dimensional array of cavities with a plurality of cavities 200 extending horizontally and a plurality of cavities extending vertically. One dimensional array 600 (FIG. 11) and two dimension array 700 (FIG. 12) can have the cross-section of an optical cavity as shown in FIG. 2 and can be formed by scaling up a fabrication process for fabricating the cavity as described with reference to FIG. 2.

Figure 13:
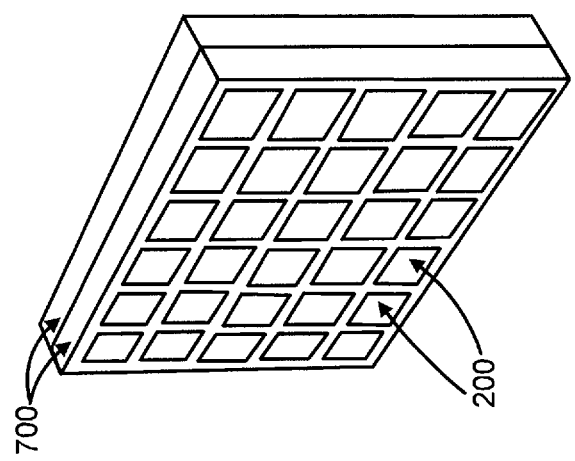
FIG. 13 is a schematic view of an optomechanical device including a plurality of stacked arrays.

In another aspect as is illustrated in FIG. 13, a plurality of arrays 700 can be configured in a series (stacked) configuration (FIG. 13 illustrates the case of plurality of stacked two dimensional arrays 700). In a stacked configuration, axes of adjacent ones of arrays 700 can be aligned. Stacking of arrays can increase a transmittivity wavelength band of an optical system.

Regarding the low power pass (power limiter) embodiment of FIGS. 4 and 5, such an optomechanical device among numerous other uses can be utilized for providing eye protection to persons who may be exposed to otherwise harmful light beams. The optomechanical device of FIGS. 4 and 5 can be configured to provide power sensitive transmittivity and reflectivity with respect to incident light having the central wavelength for which the device is to provide protection. For example, where optomechanical device 100 is to provide protection relative to a green emitting light source, optomechanical device 100 can be configured to provide appropriate power sensitive transmittivity at about the emitted central wavelength of the light source within the green band.

Figure 14:
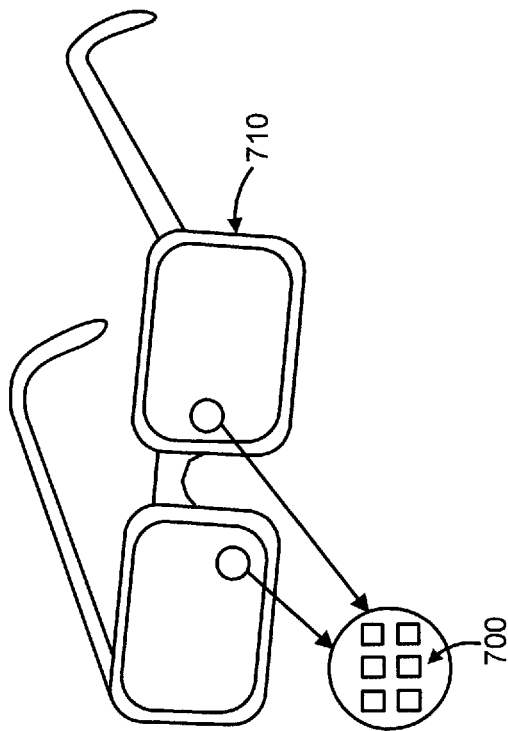
FIG. 14 is a perspective view of an optomechanical device including an eyewear apparatus incorporating an optical cavity.

In FIG. 14, there is shown optomechanical device adapted for providing eye protection. Optomechanical device 100 as shown in the embodiment of FIG. 14 can incorporate an array 700 to provide eye protection over a large two dimensional area of emitted light for which eye protection is to be provided. In the embodiment of FIG. 14, optomechanical device 100 can be configured as an eyewear apparatus. In the embodiment of FIG. 14, optomechanical device 100 can include eyewear apparatus frame 710 that supports array 700, and which accordingly supports a plurality of cavities 200. Frame 710, in one embodiment, can incorporate a stacked array as shown in FIG. 13. Shown in the form of protective eyeglasses, an eyewear apparatus incorporating cavity 200 can also include, e.g., a visor, goggles, or a shield each having an associated eyewear apparatus frame (but of different configuration than that shown in FIG. 14) which can support a cavity 200.

Another embodiment of optomechanical device 100 is described with reference to FIGS. 15-16. In the embodiment of FIGS. 15-16, cavity 200 is provided as an in-plane optomechanical device having an in-plane device structure. In the embodiment of FIGS. 15-16, first mirror 110 and second mirror 120 can be provided by drop rings. First mirror 110 and second mirror 120 as shown in FIGS. 15-16 are shown as being provided in a common plane. First mirror 110 can be made moveable by appropriate sizing of first mirror 110 as seen in FIGS. 15-16. In another aspect, optomechanical device 100 can include first waveguide 180 optically coupled to a first set of lateral edges of first mirror 110 and second mirror 120, and an oppositely disposed second waveguide 190 can be optically coupled to a second set of lateral edges of first mirror 110 and second mirror 120. Optomechanical device 100 can also include stop 70 for stopping of moveable mirror 110. Mirrors 110, 120 can include transmittivity characteristics such that mirrors 110, 120 are reflective with respect to a certain band of incident light and transmittive with respect to light outside the certain band. When forward light (moving left to right in FIGS. 15-16) is input into cavity 200 through first waveguide 180 with a central wavelength matched the reflective bands of first mirror 110 and second mirror 120, light can be reflected between first mirror 110 and second mirror 120 resulting in radiation buildup within cavity 200. Like the embodiments of FIGS. 1, 3, 5, 7, and 9 herein forward propagating light incident on cavity 200 can result in a different net force on mirror 110 than backward light yielding non-reciprocal behavior of cavity 200 and optomechanical device 100.

An excerpt is presented herein from U.S. Provisional Patent Application No. 61/153,913 with minor formatting changes and with reference numerals changed to avoid duplication.

[Excerpt taken from U.S. Provisional Patent Application No. 61/153,913].

There are described non reciprocal optomechanical devices which define a new class of optical functionalities in micro-photonics such as isolators, circulators, in-line reflection sensors, saturable absorbers, and power limiters. There is also described an optomechanical system where dominant light-matter interaction takes place via linear momentum exchange between light and the mechanical structure leading to a non-reciprocal behavior. There is further described a device that exhibits different optical behavior for a probe beam for forward and backward propagating pump beams. In one described embodiment, non-reciprocal behavior can be observed in the limit of a strong probe. There are further described planar and non-planar optomechanical devices that can exhibit this behavior in a micro photonic platform. A class of devices is described that can enable new functionalities for integrated optical systems.

Details of the above described embodiments and additional embodiments are set forth in the manuscript entitled "Optical Non-Reciprocity in Optomechanical Structures" which is attached hereto as Appendix A and which forms part of the present disclosure and in the manuscript entitled "Optomechanical Non-Reciprocal Device" which is attached hereto as Appendix B and which also forms part of the present disclosure.

[The following section is excerpted from Appendix A of U.S. Provisional Patent Application No. 61/153,913]

Breaking the reciprocity of light on-chip can lead to an important new class of optical devices such as isolators, which are critical for the development of photonic systems. Traditional methods for creating non-reciprocal devices rely on magneto-optic media, optically-active media or photovoltaic electro-optic crystals (P. S. Pershan, "Magneto-Optical Effects,"/. Appl. Phys. 38, 1482 (1967); J. Fujita, M. Levy, R. M. Osgood, Jr., L. Wilkens, and H. Dotsch, "Waveguide optical isolator based on Mach-Zehnder interferometer", Appl. Phys. Lett. 76, 2158 (2000); D. C. Jones, G. Cook, "Nonreciprocal transmission through photorefractive crystals in the transient regime using reflection geometry," Opt. Commun. 180 391-402 2000; R. J. Potton, "Reciprocity in optics," Rep. Prog. Phys. 67, 717-754 (2004)). Non-reciprocal behaviour has also been studied in time varying media (D. M. Shupe, "Thermally induced non-reciprocity in the fiber-optic interferometer," Appl. Opt. 19, 654-655 (1980); Z, Yu, and S. Fan, "Complete optical isolation created by indirect interband photonic transitions," Nature Photonics 2009. Advanced online publication doi:10.1038/nphoton.2008.273), bi-anisotropic media (Bianisotropic media are the most general linear complex media where the constitutive relationships are defined by 4 second rank tensors as $$D = \varepsilon_0(\varepsilon \cdot E + \eta_0 \xi \cdot H), B = \frac{1}{c_0}(\zeta \cdot E + \eta_0 \mu \cdot H)$$ [Eq. 3]

where D, E, B and H are the macroscopic electromagnetic fields; J. A. Kong, "Theorems of bianisotropic media," Proc. IEEE, Vol. 60, No. 9 Sep. 1972)) (such as magneto-electric media), and relativistic moving media (A. Sommerfeld, Electrodynamics. New York: Academic Press, 1952 Page 280). However, the development of non-reciprocal devices for a micro-photonic platform remains a challenge (Z, Yu, and S. Fan, "Complete optical isolation created by indirect interband photonic transitions," Nature Photonics 2009. Advanced online publication doi:10.1038/nphoton.2008.273). Hence, it is of great interest to pursue alternative mechanisms to break the reciprocity of light on a micro-scale platform. Here, we show non-reciprocity by exploiting a fundamental difference between forward and back moving light: its momentum. Recent work in optomechanics (T. J. Kippenberg and K. J. Vahala, "Cavity Opto-Mechanics," Opt. Express 15, 17172-17205 (2007), enabled by advances in optical micro cavities (K. J. Vahala, "Optical microcavities," Nature 424(6950), 839-846 (2003) and nano-electro-mechanical systems (H. G. Craighead, "Nanoelectromechanical systems," Science 290 (5496), 1532-1535 (2000), has shown tremendous potential for a new class of micro-scale devices (T. Cannon, H. Rokhsari, L. Yang, T. J. Kippenberg, K. J. Vahala, Temporal Behavior of Radiation-Pressure-Induced Vibrations of an Optical Microcavity Phonon Mode, Phys. Rev. Lett. 94, 223902 (2005); M. L. Povinelli, J. M. Johnson, M. Loncar, M. Ibanescu, E. J. Smythe, F. Capasso, and J. D. Joannopoulos, "High-Q enhancement of attractive and repulsive optical forces between coupled whispering-gallery-mode resonators," Optics Express 13(20), 8286-8295 (2005); M. Eichenfeld, C. Michael, R. Perahia, and O. Painter, "Actuation of Micro-Optomechanical Systems Via Cavity-Enhanced Optical Dipole Forces," Nature Photonics 1(7), 416 (2007); P. T. Rakich, M. A. Popovic, M. SolJ acic, E. P. Ippen. "Trapping, corralling and spectral bonding of optical resonances through optically induced potentials", Nature Photonics 1 (11), 2007, p. 658; Wiederhecker, G. S., Chen, L., Gondarenko, A. and Lipson, M., Controlling photonic structures using optical forces, Arxiv 0904.0794v1) and novel physical phenomena such as optomechanical cooling (K. C. Schwab and M. L. Roukes, "Putting mechanics into quantum mechanics," Physics Today 58(7), 36-42 (2005); V. B. Braginsky and S. P. Vyatchanin, "Low quantum noise tranquilizer for Fabry-Perot interferometer," Physics Letters A 293(5-6), 228-234 (2002); M. D. LaHaye, O. Buu, B. Camarota, and K. C. Schwab, "Approaching the quantum limit of a nanomechanical resonator," Science 304(5667), 74-77 (2004); A. Naik, O. Buu, M. D. LaHaye, A. D. Armour, A. A. Clerk, M. P. Blencowe, and K. C. Schwab, "Cooling a nanomechanical resonator with quantum back-action," Nature 443(7108), 193-196 (2006); O. Arcizet, P. F. Cohadon, T. Briant, M. Pinard, and A. Heidmann, "Radiation-pressure cooling and optomechanical instability of a micromirror," Nature 444(7115), 71-74 (2006); M. Li, W. H. P. Pernice, C. Xiong, T. Baehr-Jones, M. Hochberg, H. X. Tang, Nature 456, 480-484 (2008)). In this paper, we show that when the dominant light-matter interaction takes place via momentum exchange, optomechanical devices can exhibit non-reciprocal behaviour; since their optical spectral characteristics are strongly dependent upon the direction of the incidence of light. We propose a silicon based micro-optomechanical device that exhibits a non-reciprocal behaviour with a contrast ratio>20 dB.

Figure 17:
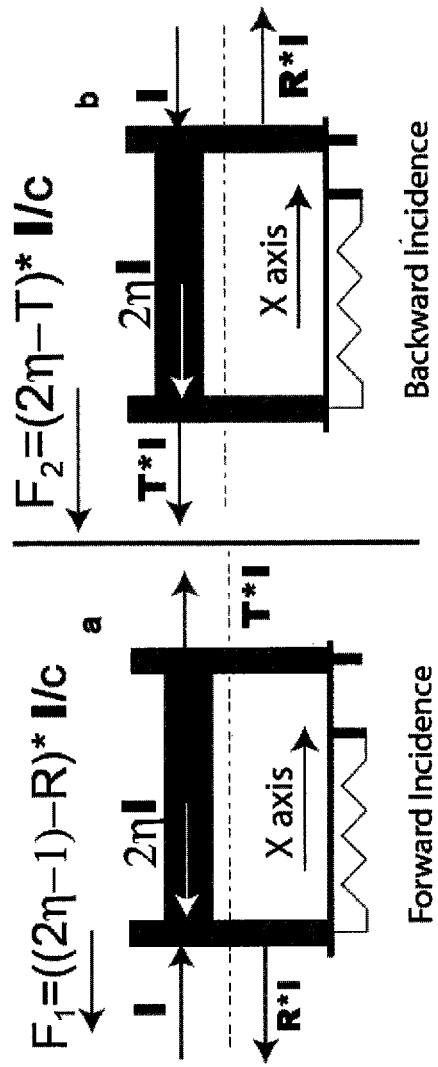
FIG. 17 shows an optomechanical scheme set forth herein, non-reciprocal response.

An example of an optomechanical structure which interacts with light through linear momentum exchange consists of an in-line Fabry Perot (FP) cavity with one movable mirror and one fixed mirror (FIG. 17). The emergence of non-reciprocity in such as system can be understood as follows (see FIG. 17, left diagram): For a left-incident beam at the optical resonance frequency, the net momentum imparted per second on the movable mirror is $-((2//-I)-R)I/c$ (where $\eta$ is the power build up factor of the cavity, R is the power reflectivity of the FP cavity, / is the incident power and c the speed of light in vacuum, and the negative sign indicates that the direction of the force is away from the cavity). On the other hand, for a right-incident beam the net momentum imparted per second on the movable mirror is $-((2\eta-1)+R)Vc$. Hence the differential radiation force for left and right incident beams is $2RI/c$ producing a non-reciprocal mechanical response from the mirror leading to non-reciprocal optical transmission spectra.

Figure 18:
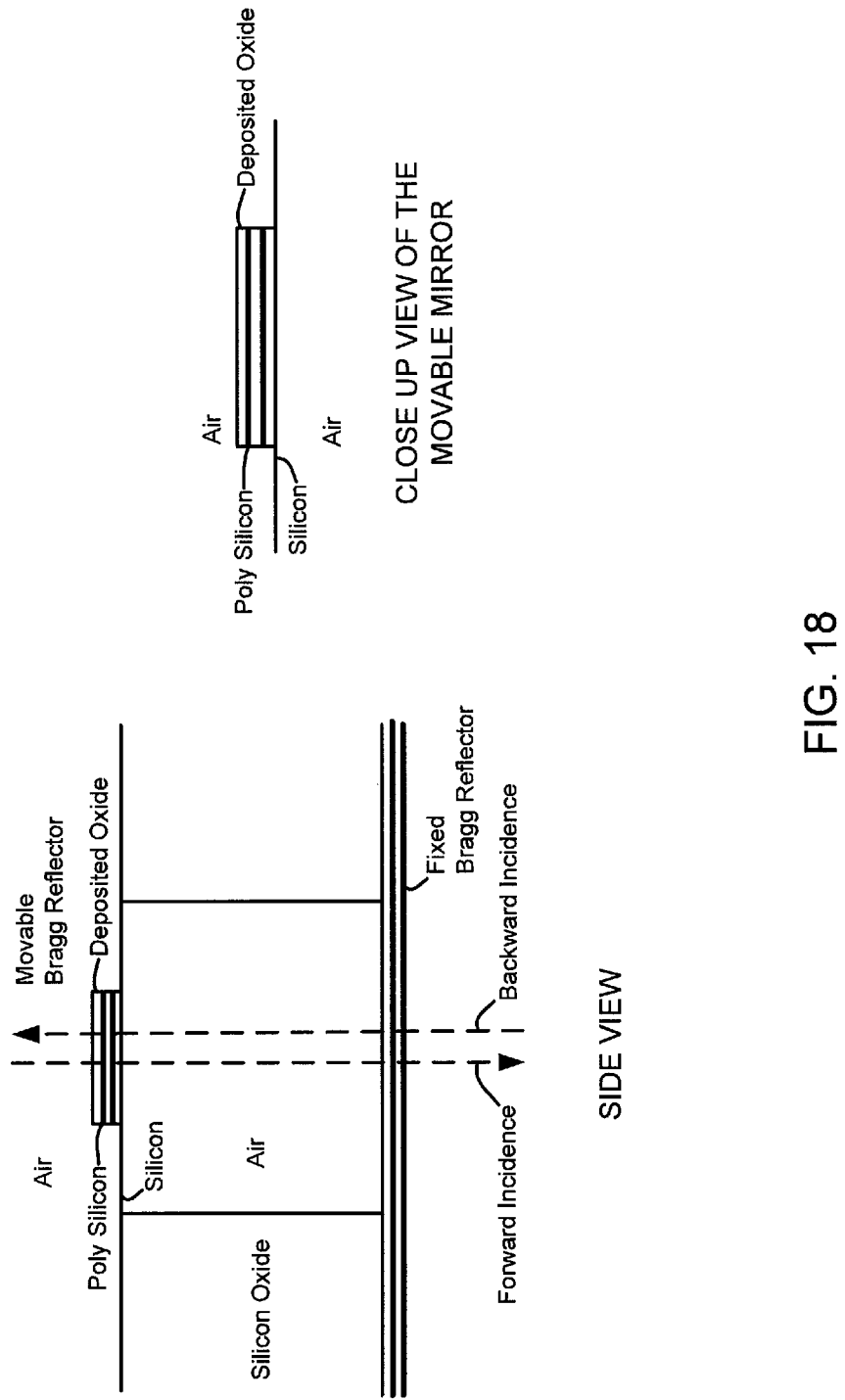
FIG. 18 shows a side view of an optomechanical device for realizing non-reciprocal transmission spectra.
Figure 20:
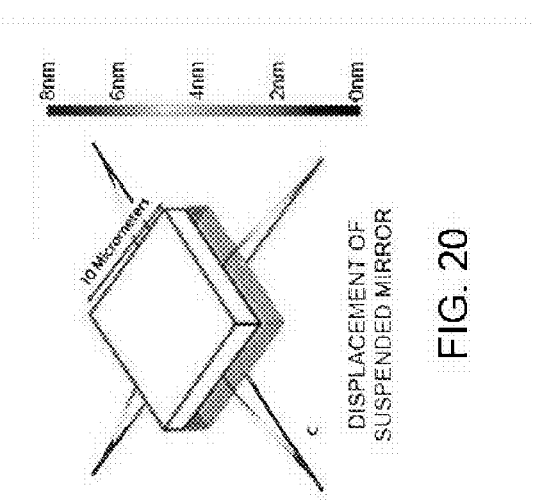
FIG. 20 is a diagram showing a mechanical response of the suspended mirror for a radiation force corresponding to 100 mW incident power.
Figure 19:
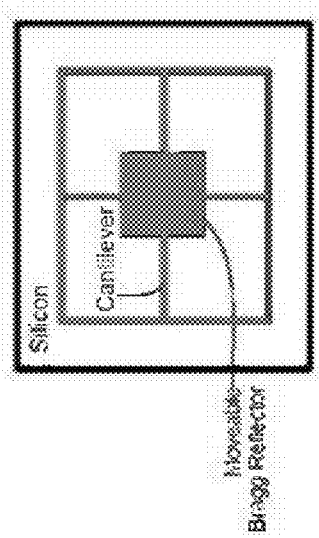
FIG. 19 shows a top view of the optomechanical device of FIG. 20.
Figure 21:
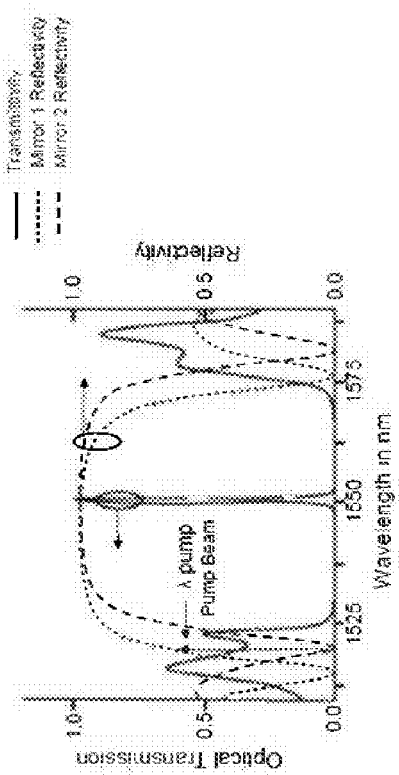
FIG. 21 shows an optical transmission through the device for low light intensities. Reflectivity spectra for the mirrors are shown in dotted lines. Layer thicknesses of the mirrors are slightly offset (5 nm) to allow for a pump probe measurements.

To illustrate the non-reciprocal behavior in a realistic micro-optomechanical device we describe a representative device which can be fabricated in a silicon material system. The device (FIG. 18) consists of a quasi-ID standing wave cavity formed by two quarter wave Bragg reflectors with one of the mirrors suspended via micro-cantilevers (B. Ilic, H. G. Craighead, S. Krylov, W. Senaratne, C. Ober, P. Neuzil, "Attogram Detection Using Nanoelectromechanical Oscillators", Journal of Applied Physics, 95, 3694-3703 (2004)). The mirrors forming the cavity are fabricated in a high index contrast system (the refractive indices of Si and $SiO_2$ are approximately 3.5 and 1.5 respectively). Spring constants spanning several orders of magnitude can be achieved (typically from $10"Nm^{-1}$ to $1 Nm^{-1}$ [24]), by varying the materials, geometry and the arrangement of the cantilevers. We model the movable mirror as a vertical translation plate supported by four beams. Using COMSOL (M. Bao, H. Yang, "Squeeze film air damping in MEMS", Sensors and Actuators A 136 (2007) 3-27) software package we compute the mechanical response of the structure by including material properties and boundary conditions into a Finite Element Method (FEM) based solver. No angular displacement is allowed because the beams are connected to the mirror which remains parallel to the substrate under nominal plate movements. The spring constant associated with four fixed beams is given by $4Ewt^3/l^3$ where E is the young's modulus and w, t, and/are the width, thickness, and length of the silicon beams respectively (www.comsol.com). In a given material system, the cubic dependence of the spring constant on the aspect ratio (t/l) allows for a wide range of spring constants for this beam geometry. We consider a $10\times10\,\mu m^2$ mirror suspended using micro-cantilevers of thickness 110.5 nm {~$\lambda JAn_{si}$ where $\lambda_c$ is 1550.5 nm and $n_{si}$ (3.5) the refractive index of silicon}, 10 μm length, and 100 nm width. The mass of the mirror is 165.26 pg. The spring constant for the chosen dimensions is $0.06\,Nm^{-1}$. Using the FEM software we calculate the mechanical displacement of the movable mirror for −666 pN (2I/c) applied force corresponding to a net radiation force from a 100 mW beam reflected perfectly from the mirror (see FIG. 18) to be on the order of 10 nm. The bandwidth of the optical cavity formed by the mirrors is primarily determined by the reflectivity of the mirrors. We show the optical transmission characteristics of the device in FIG. 21. We consider quarter wave stacks on either side formed by alternating layers of Si and $SiO_2$ with 2 layers of deposited silicon and three layers of deposited oxide. The mirrors form an air filled cavity of length ~$5(M_c/2$. The quality factor of the cavity [$Q=X_0 ZAX$) is ~5200 centred at ~$\Lambda_c$=1550.5 nm. The mirror layers have thicknesses of $21\lambda_{mirror1}/4\,n_{si}$, $21\lambda_{mirror2}/4\,n_{si}$.

Figure 22:
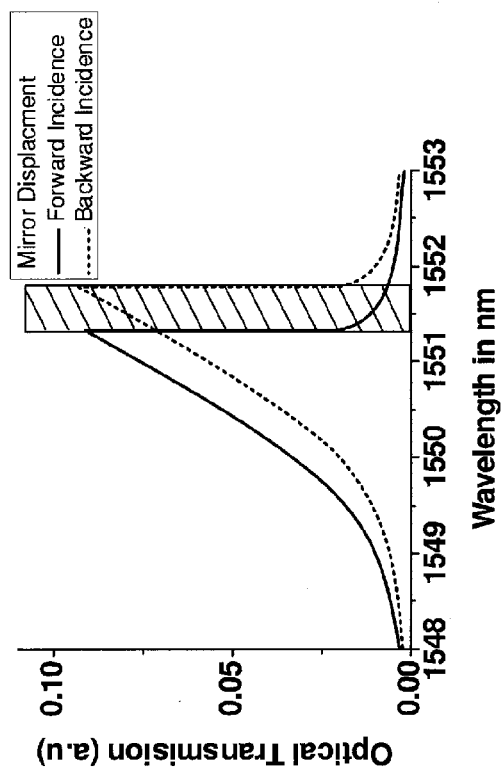
FIG. 22 shows transmission spectra of the device for forward and backward incidence of light.
Figure 23:
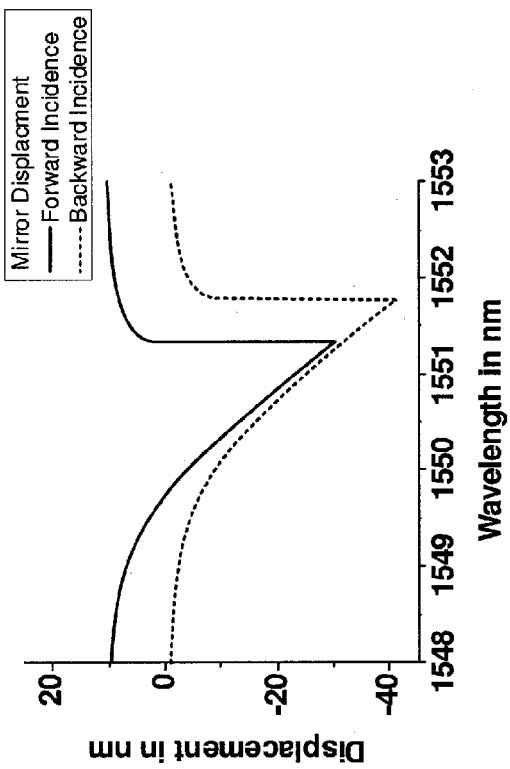
FIG. 23 shows a steady state displacement of the movable mirror for forward and backward incidence of light.

Non-reciprocal behavior in the proposed structure emerges due to the asymmetry of the radiation pressure on the movable mirror for forward and backward incident light. We model the cantilever dynamics by a driven second order differential system with a non-linear driving function $$\frac{d^2 x}{dt^2} + \frac{b}{m_{eff}}\frac{dx}{dt} + \frac{K}{m_{eff}} x = \frac{F_{RP}(\lambda, x, t)}{m_{eff}} \quad [\text{Eq. 4}]$$

where radiation force on die movable mirror is $$F_{RP}(\lambda, x, t) = \begin{bmatrix} -((2\eta-1) - R(\lambda, x, t))*I/c & \text{for forward incidence} \\ -(2\eta-1 + R(\lambda, x, t))*I/c & \text{for backward incidence} \end{bmatrix} \quad (2)$$

where I is the power of the incident beam η, R are the intensity build up factor, and reflectivity of the cavity for wavelength λ and movable mirror position x. The position dependent reflectivity $R(\lambda, x, t)$ is given as a function of displacement x as, $$R(\lambda, x, t) = 1 - \left[\left(\frac{|t_1 t_2|}{1-|r_1 r_2|}\right)^2 \frac{1}{1+4\left(\frac{\sqrt{|r_1 r_2|}}{1-|r_1 r_2|}\right)^2 \sin^2 \varphi(x)}\right]^{1/2} \quad [\text{Eq. 5}]$$

where φ(x) is the phase shift per round trip inside the cavity:

$$\frac{1}{2}\text{Arg}\left[r_1 r_2 e^{i\frac{2\pi}{\lambda}(l-x)}\right]$$

and $r_1$, $r_2$ & $t_1$, $t_2$ are the mirror reflectivties and trasnmittivities; / is the steady state cavity length. We assume a mass of 165.26 pg, spring constant of $0.06\,Nm^{-1}$ (corresponding to a $10\times10\,\mu m^2$ Bragg mirror, see FIGS. 18-21) and a net damping parameter of $10^{-6}\,kgs^{-1}$. The damping mechanisms may include mass damping, stiffness damping, acoustic leakage at the anchors and thin fluid squeezing (M. Bao, H. Yang, "Squeeze film air damping in MEMS", Sensors and Actuators A 136 (2007) 3-27). The coupled optomechanical response is calculated at each time step (1 ns~$\tau_{mechamca}i/1600$) by updating both the optical and mechanical state of the cavity. We also note that the photon life time ($\tau_{Ph_0}tO_n$=A.Q/2πc~4.1 ps) is much smaller than the mechanical rise time ($\tau_{mech}a_m$cai=b/m~\6 ns), which allows for the calculation of the optomechanical response iteratively. We neglect the quantum Langevin noise in calculating the optomechanical response. The transmission spectral characteristics exhibit the classical behaviour of optical bi-stable systems. The transmission spectra of the device for forward and backward incident light are shown in FIGS. 22-23. One can see the formation of a non-reciprocal transmission window at 1551.2 nm with a bandwidth of 0.25 nm and a forward to backward incident light extinction ratio of >16 dB. The transition time for backward to forward incidence (and vice versa) is on the order of ($\approx(\frac{1}{2}Q_m)*(\sqrt{K/m_{eff}})$, where $Q_{1n}$ is the mechanical quality factor) given by mechanical design of the movable mirror.

Figure 24:
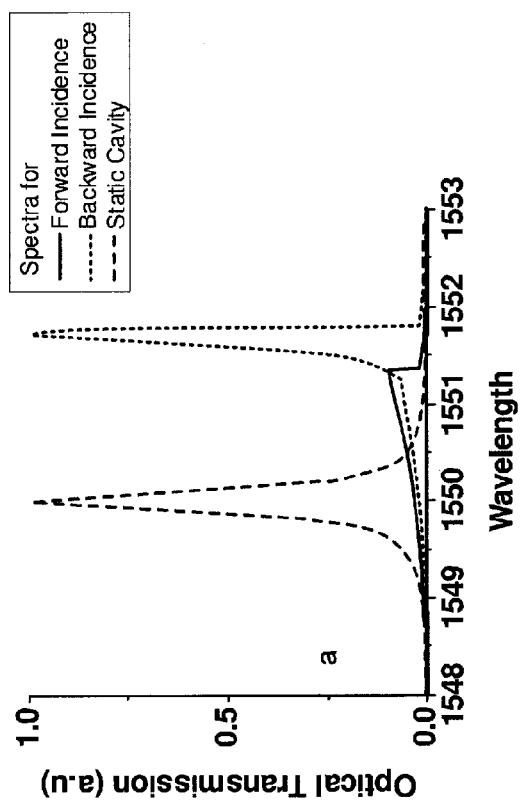
FIG. 24 shows transmission spectra of the proposed device for forward and backward incidence of light when the movable mirror is constrained at 30 nm displacement to achieve stability on resonance.
Figure 25:
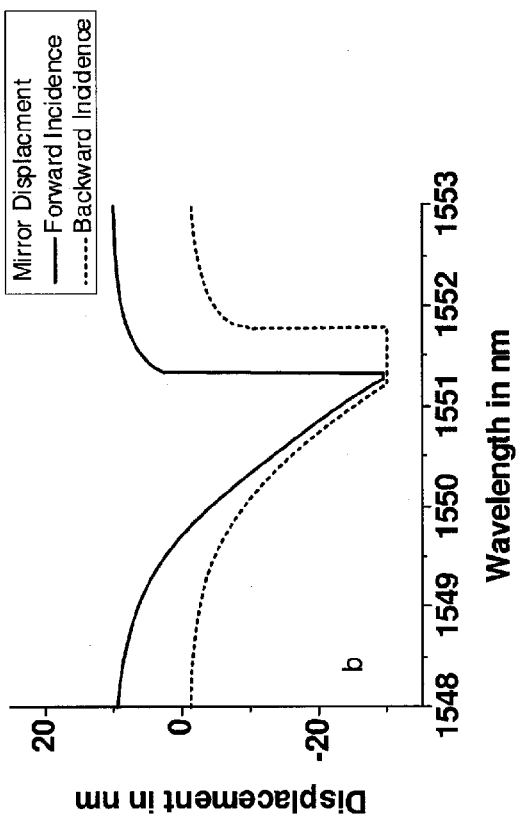
FIG. 25 shows mirror displacements for forward and backward incident light.

The insertion loss through the device can be minimized by providing a mechanical stop for the movable mirror. To obtain a unity peak transmission, the FP cavity needs to be perfectly on resonance with the incoming light. However when the cavity is perfectly on resonance, the radiation force on the mirror passes through a maximum leading to instability (T. Carmon, H. Rokhsari, L. Yang, T. J. Kippenberg, K. J. Vahala, Temporal Behavior of Radiation-Pressure-Induced Vibrations of an Optical Microcavity Phonon Mode, Phys. Rev. Lett. 94, 223902 (2005)). A mechanical stop allows for peak resonance build up while producing a non reciprocal response. We describe a non-reciprocal optomechanical device to achieve low insertion loss (<0.1 dB), high forward to backward incidence extinction ratio (>20 dB). In FIG. 24, we show the transmission spectra for forward and back ward incident light of 100 mW power when the mirror is constrained to −30 nm displacement. One can see the formation of a non-reciprocal spectrum with a 0.25 nm bandwidth and a forward to back ward light extinction ratio>20 dB. The insertion loss for the backward light is now <0.1 dB. The bandwidth of the non-reciprocal spectrum can be controlled by choosing the appropriate mirror reflectivity. We note that an important consideration for a mechanical stop is the affect of stiction force for mechanical objects in close proximity. However earlier works have successfully demonstrated various methods to overcomes this problem (Maboudian, R., W. R. Ashurst and C. Carraro, Tribological challenges in micromechanical systems. 12 (2002) 95; R. Maboudian and R. T. Howe, Stiction reduction processes for surface micromachines. Tribol. Lett. 3 (1997), p. 215).

The thermal equipartition noise imposes a minimum power condition for observing the non-reciprocal behavior. We estimate the optical power required for the radiation force displacement to exceed the mean square displacement of the mirror for a given spring constant. The minimum optical power required to overcome the thermal position noise is given by $I_{min}=cK\Delta x$, where $\Delta x_{min}=\sqrt{kT/K}$, k the Boltzmann constant, K the spring constant, and T=300 K ambient temperature. Following the fluctuation dissipation theorem, this analysis takes into account the Langevin noise (Kubo, R. The fluctuation-dissipation theorem. Rep. Prog. Phys. 29, 255-284 (1966)). One can see that the net optical power contributing to the non-reciprocal behaviour should be in the range of 10's of mW to overcome the thermal equipartition noise. The optical power $I_{min}$ can be lowered by lowering the spring constant. Even though thermal non-linearity has traditionally been an important constraint to micro-photonic devices (Cannon, T., Yang, L. & Vahala, KJ. "Dynamical thermal behaviour and thermal selfstability of microcavities". Optics Express 12, 4742 (2004)), we note that the effect of thermal non-linearity will only contribute equally to both directions of incidence. The general principles described here for creating devices with non-reciprocal transmission spectra can be extended to in-plane geometry by employing suspended resonators (L. Martinez and M. Lipson, "High confinement suspended micro-ring resonators in silicon-on-insulator," Opt. Express 14, 6259-6263 (2006)) as frequency selective reflectors (S. Manipatruni, P. Dong, Q. Xu, and M. Lipson, "Tunable superluminal propagation on a silicon microchip," Opt. Lett. 33, 2928-2930 (2008). This class of devices with non-reciprocal spectra can enable new functionalities for integrated optical systems.

[End of Section Excerpted as Appendix A of U.S. Provisional Patent Application No. 61/153,913]

[The Following Section Is Excerpted From Appendix B of U.S. Provisional Patent Application No. 61/153,913]

Recent work in optomechanics (T. J. Kippenberg and K. J. Vahala, "Cavity Opto-Mechanics," Opt. Express 15, 17172-17205 (2007)), enabled by advances in optical micro cavities (K. J. Vahala, "Optical microcavities," Nature 424(6950), 839-846 (2003)) and nano-electromechanical systems (H. G. Craighead, "Nanoelectromechanical systems," Science 290 (5496), 1532-1535 (2000)), has shown tremendous potential for new classes of micro scale devices (T. J. Kippenberg, H. Rokhsari, T. Carmon, A. Scherer, and K. J. Vahala, "Analysis of Radiation-Pressure Induced Mechanical Oscillation of an Optical Microcavity," Physical Review Letters 95, 033,901 (2005), M. Hossein-Zadeh and K. J. Vahala, "Photonic RF Down-Converter Based on Optomechanical Oscillation," Photonics Technology Letters, IEEE, 20, Issue 4, Page(s): 234-236 (2008), M. L. Povinelli, J. M. Johnson, M. Loncar, M. Ibanescu, E. J. Smythe, F. Capasso, and J. D. Joannopoulos, "High-Q enhancement of attractive and repulsive optical forces between coupled whispering-gallery-mode resonators," Optics Express 13(20), 8286-8295 (2005), M. Eichenfeld, C. Michael, R. Perahia, and O. Painter, "Actuation of Micro-Optomechanical Systems Via Cavity-Enhanced Optical Dipole Forces," Nature Photonics 1(7), 416 (2007), O. Arcizet, P. F. Cohadon, T. Briant, M. Pinard, A. Heidmann, J. M. Mackowski, C. Michel, L. Pinard, O. Francais, and L. Rousseau, "High-sensitivity optical monitoring of a micromechanical resonator with a quantum limited optomechanical sensor," Physical Review Letters 97(13), 133,601 (2006), P. T. Rakich, M. A. Popovic, M. Soljacic, E. P. Ippen. "Trapping, corralling and spectral bonding of optical resonances through optically induced potentials", Nature Photonics 1 (11), 2007, p. 658) and phenomena K. C. Schwab and M. L. Roukes, "Putting mechanics into quantum mechanics," Physics Today 58(7), 36-42 (2005)). In this paper, we show that, when dominant light matter interaction takes place via linear momentum exchange, it can lead to a non reciprocal behavior where device optical spectral characteristics are modified strongly depending up on the direction of incidence of light.

Breaking the reciprocity of light can lead to a new class of on-chip optical devices such as optical isolators and circulators with functionalities complementary to reciprocal optical devices such as modulators, filters, and switches. Traditional methods for non reciprocal devices rely on magneto-optic media, optically active media, or photovoltaic electrooptic crystals. (P. S. Pershan, "Magneto-Optical Effects," J. Appl. Phys. 38, 1482 (1967), J. Fujita, M. Levy, R. M. Osgood, Jr., L. Wilkens, and H. Dotsch, "Waveguide optical isolator based on Mach-Zehnder interferometer," Appl. Phys. Lett. 76, 2158 (2000), and D. C. Jones, G. Cook, "Nonreciprocal transmission through photorefractive crystals in the transient regime using reflection geometry," Opt. Commun. 180 391-402 2000).

All these materials are hard to integrate on a CMOS compatible micro-scale platform which has emerged as a strong candidate for micro photonics. Hence, it is of great interest to pursue alternative mechanisms to break the reciprocity of light on a micro scale platform.

Devices described herein can enable non reciprocal effects (i.e., left and right moving light see different optical effects from an optical system) on an integrated photonics chip. Devices described herein also can provide different optical response for forward (left) and backward (right) propagating optical signals. Devices described herein also can sense presence of a strong optical beam forward or backward and produces distinguishable responses. Devices described herein also can act as an optical isolator for strong optical signals. Devices described herein also can operate without the use of magneto-optic media, optically active media, or photovoltaic electrooptic crystals. Devices described herein also can be operated as a saturable absorber or a saturable power limiter. Devices described herein also can be operated as a saturable absorber for use in pulses laser systems. Devices described herein also can be used as a safety measure to block intense light for sensitive optical systems. Devices described herein also can be fabricated in a silicon CMOS fabrication facility. The proposed device can be used as a light controlled light switch.

A fundamental difference between forward and backward propagating light is the direction of linear momentum carried by the electromagnetic field. Hence if we can design an optomechanical structure which taps the linear momentum to reconfigure the optical device, we will be able to differentiate forward and backward propagating light, thus creating non reciprocal transmission spectra. We show that the proposed device can achieve this functionality. We also propose planar and non-planar optomechanical devices which can exhibit this behavior in a micro photonic platform.

Figure 26:
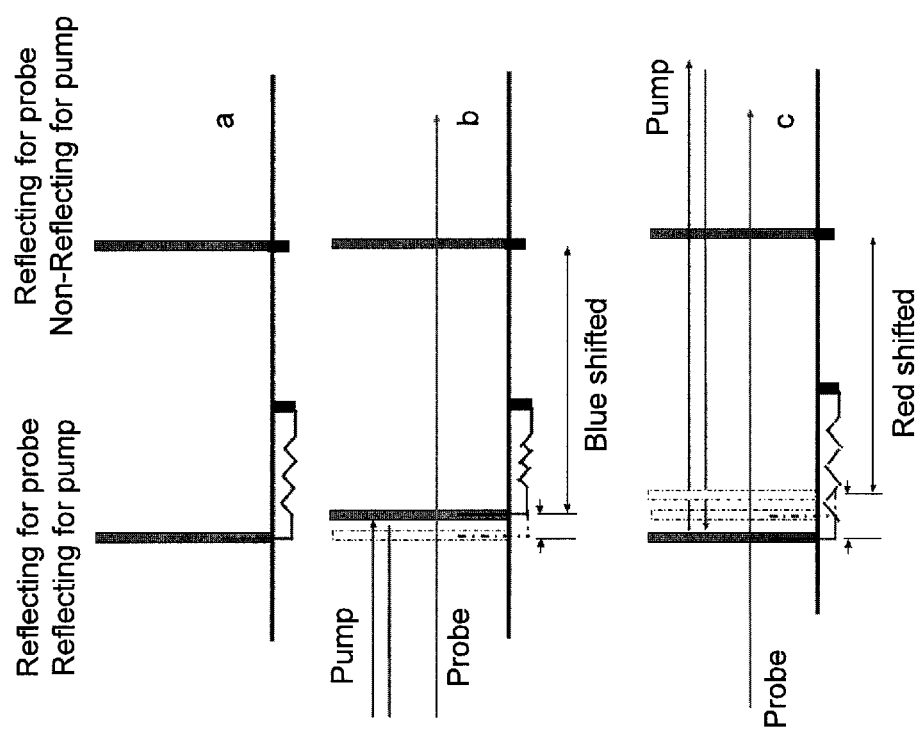
FIG. 26 shows an optomechanical structure set forth herein a Fabry-Perot (FP) cavity with one of the mirrors movable and the other fixed to the substrate. The left mirror is reflecting for the pump and probe. The right mirror is reflecting only for the probe.

In FIG. 26 there is shown an optomechanical structure under consideration. There is shown Fabry-Perot (FP) cavity with one of the mirrors movable and the other fixed to the substrate. The left mirror is reflecting for the pump and probe. The right mirror is reflecting only for the probe.

Here we introduce a general structure for creating a direction sensitive transmission spectrum using optomechanical structures. The proposed structure is an in line Fabry Perot (FP) cavity with one movable mirror and one fixed mirror (FIG. 26, top diagram). The pump signal is reflected only at the movable mirror while the probe signal is reflected both at the movable and the fixed mirror. The direction sensitive transmission spectrum is realized as follows: a) For left incident light (FIG. 26, middle diagram, when the pump is incident from the left of the FP cavity, the reflection of the incident beam produces a net momentum change of the photons to the left producing radiation pressure to the right. The cavity optical path is reduced leading to a blue shifted transmission spectrum, b) For right incident light (FIG. 26, bottom diagram), when the pump is incident from the right of the FP cavity, the incident beam interacts only with the movable mirror (by appropriate design of the fixed mirror) produces a net momentum change of the photons to the right producing radiation pressure to the left. The cavity optical path is increased leading to a red shifted transmission spectrum. In the limiting case of the probe becoming strong, the left and right incident conditions still produce different momenta on the movable mirror leading to non reciprocal transmission spectra.

Figure 27:
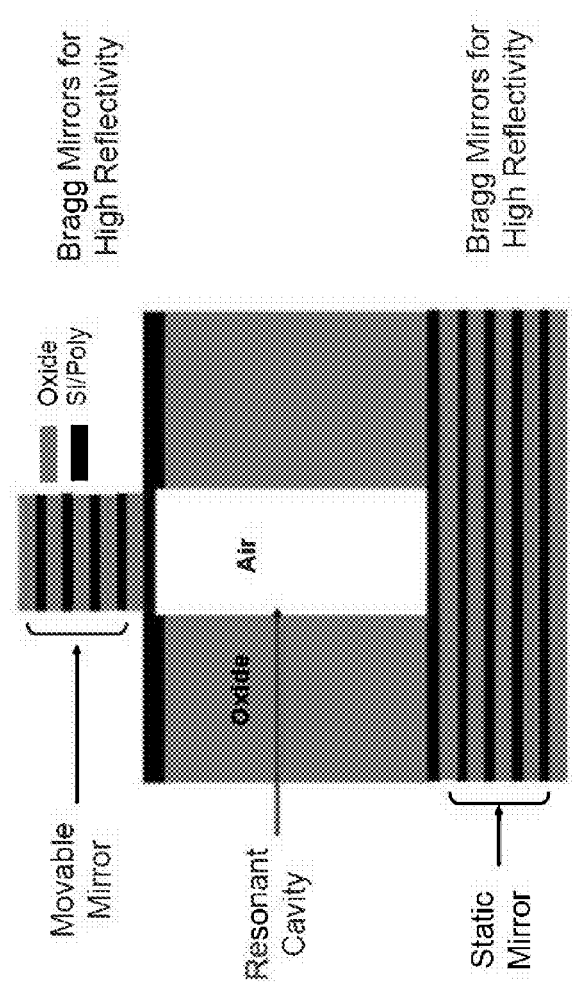
FIG. 27 shows an optomechanical device for non reciprocal transmissions quarter wave Bragy reflectors are formed at either ends of a $SiO_2$ cavity. The structure is fabricated by attaching two SOI wafers. Bragg reflectors are designed such that both the reflectors are reflective for the probe signal. Only the movable mirror is reflective for the control pump signal.

In FIG. 27, there is shown proposed optomechanical device for non reciprocal transmissions. As shown in FIG. 27, quarter wave Bragg reflectors are formed at either ends of an $SiO_2$ cavity. The structure is fabricated by attaching two SOI wafers. Bragg reflectors are designed such that both the reflectors are reflective for the probe signal. Only the movable mirror is reflective for the control pump signal.

Figure 28:
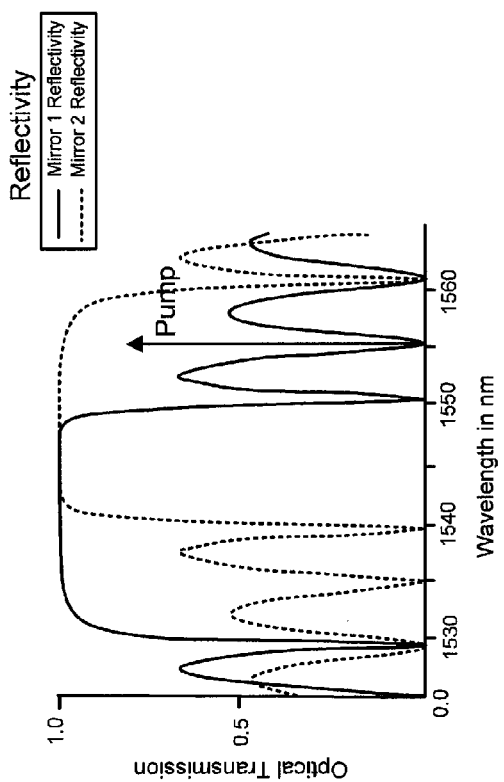
FIG. 28 shows reflectivity spectra for the mirrors. The non movable mirror is transparent to the pump beam.

We describe an optomechanical device which fulfills the characteristics for non reciprocal transmission spectra in a silicon-silicon oxide material system. The device is shown in FIG. 27. The mirrors forming the cavity are created formed in a high index contrast system (refractive index of silicon 3.5, refractive index of oxide 1.5) using a quarter wave stack. The fabrication of the proposed device is straight forward involving only lithography, etching, and deposition steps. A material stack of silicon and oxide is etched from the oxide side to create the optical cavity. Another silicon wafer is bonded to close the cavity, since there is no lithography involved on the second side of the cavity there is no need for alignment of the mirrors. Polysilicon and oxide are deposited to create Bragg reflectors with appropriate thickness. The mirror stack thicknesses are chosen such that probe is reflected at both the mirrors while the pump is reflected only at the movable mirror (FIG. 28). In the present design we consider a quarter wave stack of order 5 at both the ends and a cavity length of 100 microns.

In FIG. 28 there is shown reflectivity spectra for the mirrors. The non movable mirror is transparent to the pump beam.

Figure 29:
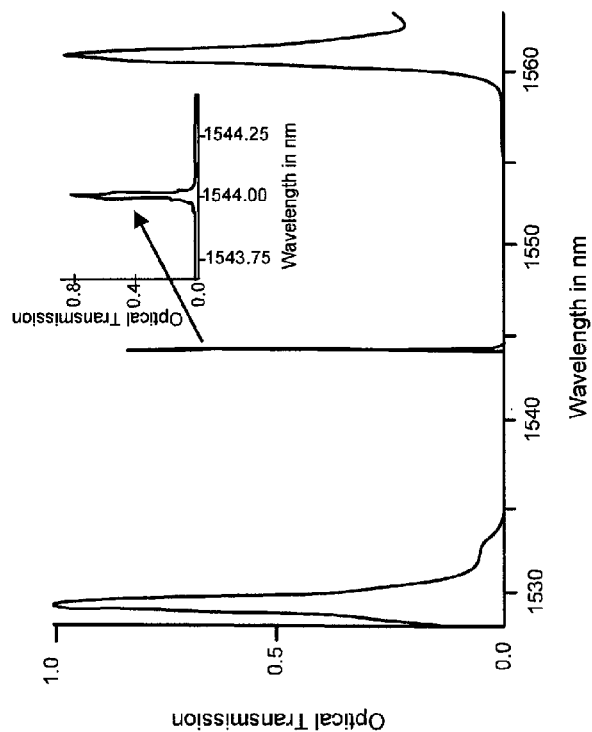
FIG. 29 shows transmission spectrum of the device under no excitation.

In FIG. 29 there is shown transmission spectrum of the device under no excitation.

Figure 31:
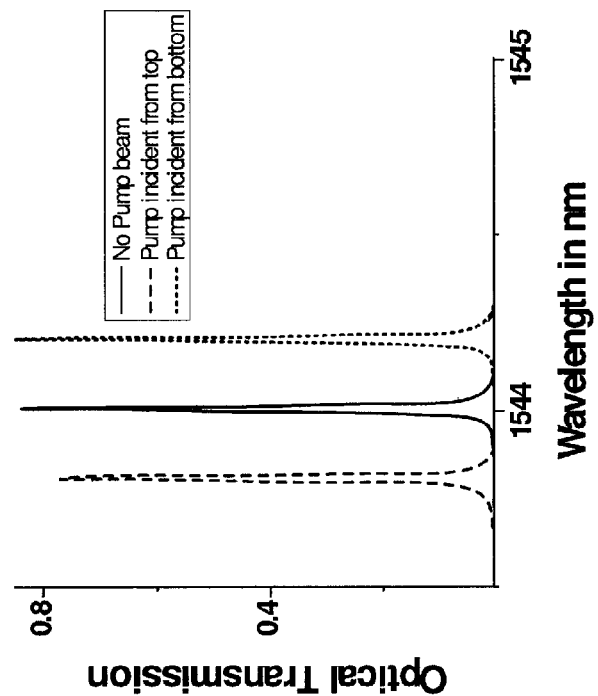
FIG. 31 shows close up transmission spectra of the device for top (forward) and bottom (backward) incidence of pump beam. When light is incident from top, the cavity is blue shifted. When light is incident from bottom the cavity is red shifted. A shift of 10 nm is assumed consistent with the mechanical simulations.
Figure 30:
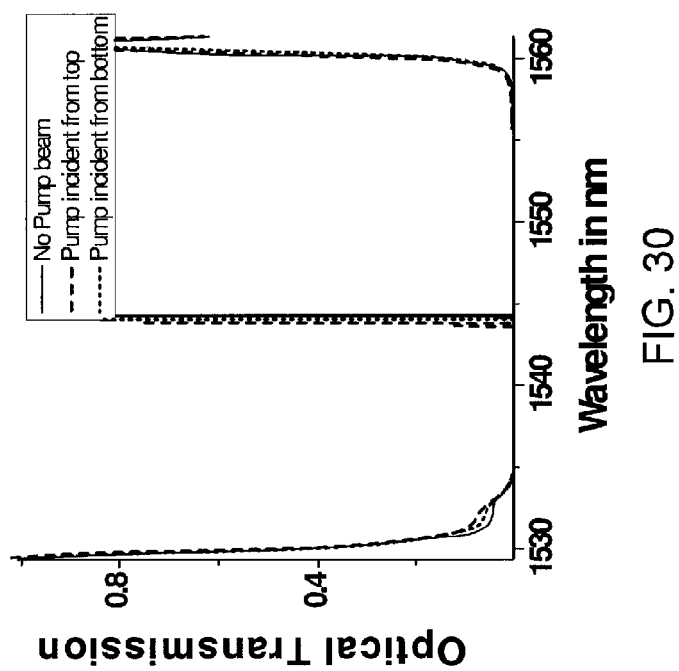
FIG. 30 shows transmission spectrum of the device for forward and backward probe beam excitation.

In FIG. 30 There is shown transmission spectrum of the device for forward and backward probe beam excitation. In FIG. 31 there is shown a close up transmission spectra of the device for top (forward) and bottom (backward) incidence of pump beam. When light is incident from top, the cavity is blue shifted. When light is incident from bottom the cavity is red shifted. A shift of 10 nm is assumed consistent with the mechanical simulations.

Figure 32:
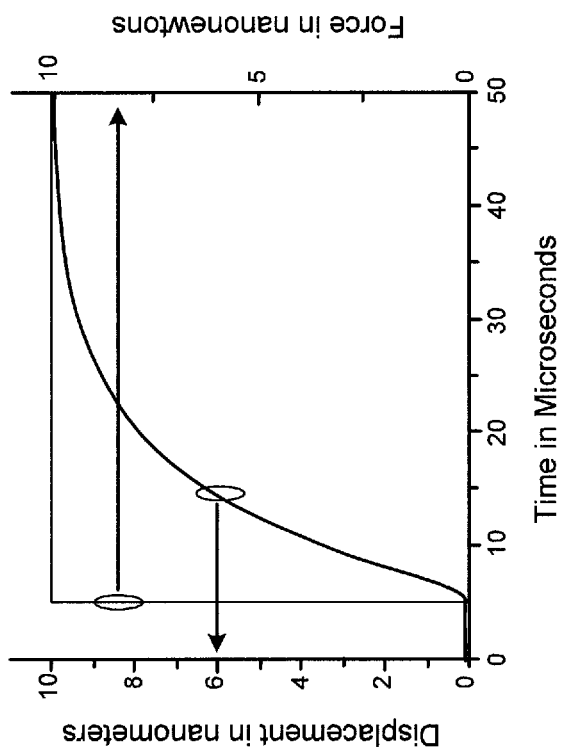
FIG. 32 shows a mechanical response of the movable mirror.

In FIG. 32 there is shown a mechanical response of the movable mirror.

We also show an in-plane alternative to the proposed invention. In an in-plane device, add drop rings (one ring resonator side coupled to two waveguides acts as a mirror by rerouting the incident light into the second waveguide. The net change of optical momentum exerts a force on the structure. By suspending the cavities on a chip we can use an add drop ring as a movable mirror. A second static mirror is created by another add drop ring which is not suspended to keep the mirror static. The principle of operation of the mirror is exactly similar to the description above.

Other alternatives may use several photonic structures (for example, toroids, rings, photonic crystals, metallic mirrors) which act as reflectors. Any method of mechanical suspension can be integrated to create the movable cavity. The methods of suspension can be mechanical, electrical, optical, magnetic levitation, micro fluidic (air or liquid).

Figure 33:
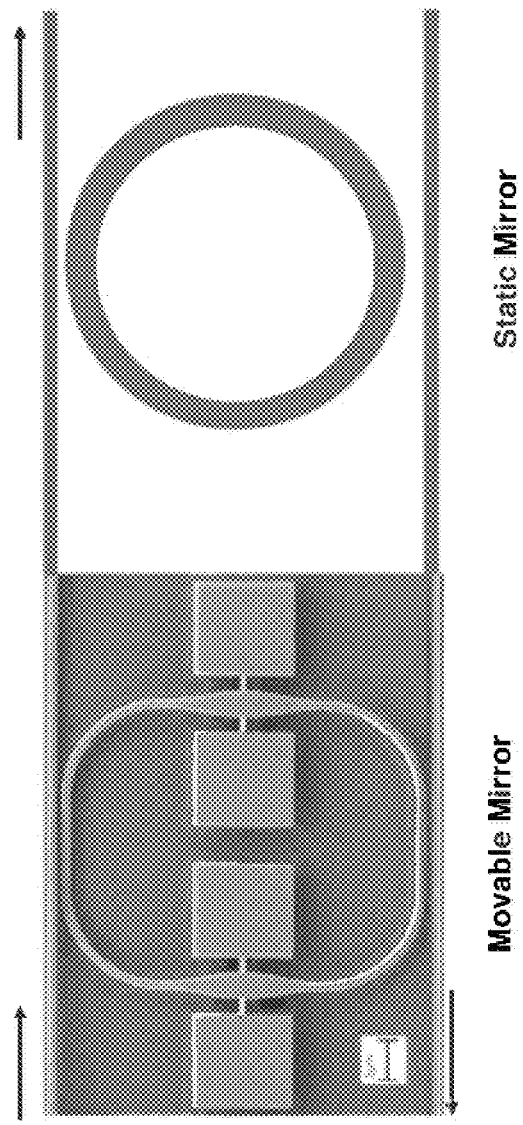
FIG. 33 shows an in-plane alternative to an optomechanical device.

In FIG. 33 there is shown an in-plane alternative to the proposed device.

There are a number of possible uses for devices described herein. Devices described herein can sense presence of a strong optical beam forward or backward and produce distinguishable responses. Devices described herein also can act as an optical isolator for strong optical signals. Devices described herein also can avoid the use of magneto-optic media, optically active media, or photovoltaic electrooptic crystals. Devices described herein also can act as a saturable absorber or a saturable power limiter. Devices described herein also can act as a saturable absorber for use in pulses laser systems. Devices described herein also can act as a safety measure to block intense light for sensitive optical systems for safety purposes. Devices described herein also can be used as a light controlled light switch. Devices described herein also can be used for intra chip, chip-chip, rack-rack, and long haul data transmission as part of an electronic, photonic, or electro-optic chip. Devices described herein also can be used in all packaged optical systems as a safety feature. Devices described herein also can be used to create military safety eye wear where strong laser beams from enemy laser weapon systems can be prevented from creating optical damage to soldiers and equipment by blocking strong light from one direction.

[End of Section Excerpted as Appendix A of U.S. Provisional Patent Application No. 61/153,913]

[End of Excerpt Taken From U.S. Provisional Patent Application No. 61/153,913]

A small sample of systems methods and apparatus that are described herein is as follows:

A1. An optomechanical device comprising: a first mirror; and a second mirror forming with the first mirror a cavity; wherein the first mirror is a movable mirror; wherein the optomechanical device is adapted so that the first mirror is moveable responsively to radiation force.

A2. The optomechanical device of A1, wherein the second mirror is a stationary mirror.

A3. The optomechanical device of A1, wherein the optomechanical device includes a mechanical stop for stopping the first mirror.

A4. The optomechanical device of A1, wherein the optomechanical device includes a mechanical stop for stopping the first mirror at a certain position to result in a certain resonance wavelength band of the cavity being defined.

A5. The optomechanical device of A1, wherein the optomechanical device is operative so that light incident on the cavity in a forward direction results in a first set of radiation forces on the first mirror, and wherein the optomechanical device is further operative so that light incident on the cavity in a backward direction results in a second set of radiation forces on the first mirror, the sum of the second set of radiation forces being different from a sum of the first set of radiation forces.

A6. The optomechanical device of A1, wherein the optomechanical device is fabricated in a solid state material system. A7. The optomechanical device A6, wherein the solid state material is fabricated in a silicon material system.

A8. The optomechanical device of A1, wherein the first mirror is made moveable with use of mechanical suspensions.

A9. The optomechanical device of A8, wherein the mechanical suspensions are provided by cantilevers.

A10. The optomechanical device of A1, wherein the optomechanical device includes a light source that emits light at a certain central wavelength, and wherein the optomechanical device is operative so that light emitted from the light source incident on the cavity in a forward direction results in a first set of radiation forces being imparted on the first mirror, and wherein the optomechanical device is further operative so that reflected light having the certain central wavelength incident on the cavity in a backward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction.

A11. The optomechanical device of A1, wherein the optomechanical device includes a light source that emits light at a certain central wavelength, and wherein the optomechanical device is operative so that light emitted from the light source incident on the cavity in a forward direction results in a first set of radiation forces being imparted on the first mirror, and wherein the optomechanical device is further operative so that reflected light having the certain central wavelength incident on the cavity in a backward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction, wherein the certain central wavelength is matched to the first resonance wavelength band but not matched to the second resonance wavelength band so that the reflected light at the certain central wavelength is not transmitted by the cavity. A12. The optomechanical device of A1, wherein the optomechanical device includes a light source that emits light at a certain central wavelength, and wherein the optomechanical device is operative so that light emitted from the light source incident on the cavity in a forward direction results in a first set of radiation forces being imparted on the first mirror, and wherein the optomechanical device is further operative so that reflected light having the certain central wavelength incident on the cavity in a backward direction simultaneously with light from the light source being incident on the cavity in the forward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction simultaneously with light from the light source being incident on the cavity in the forward direction, wherein the certain central wavelength is matched to the first resonance wavelength band but not matched to the second resonance wavelength band so that the reflected light at the certain central wavelength is not transmitted by the cavity.

A13. The optomechanical device of A1, wherein during an initial state a resonance wavelength band of the cavity is matched to a certain central wavelength so that the cavity is capable of transmitting light emitted from a light source at the certain central wavelength, and wherein the optomechanical device is adapted so that a set of radiation forces on the first mirror attributable to emission of light at the certain central wavelength with sufficient power results in a resonance wavelength band of the cavity shifting from a wavelength band at which the resonance wavelength band of the cavity is matched to the certain central wavelength to a wavelength band at which the resonance wavelength band is not matched to the certain central wavelength.

A14. The optomechanical device of A1, wherein during an initial state a resonance wavelength band of the cavity is not matched to a certain central wavelength so that in an initial state the cavity is restricted from transmitting light emitted from a light source at the certain central wavelength, and wherein the optomechanical device is adapted so that a set of radiation forces on the first mirror attributable to emission of light at the certain central wavelength with sufficient power results in a resonance wavelength band of the cavity shifting from a wavelength band at which the resonance wavelength band of the cavity is not matched to the certain central wavelength to a wavelength band at which the resonance wavelength band of the cavity is matched to the certain central wavelength.

A15. The optomechanical device of A14, wherein the optomechanical device includes a stop for stopping the first mirror at a certain position for stabilization of the resonance wavelength band at a wavelength band at which it is matched to the certain central wavelength when light having the certain central wavelength of sufficient power is incident on the cavity.

A16. The optomechanical device of A1, wherein the optomechanical device is adapted so that radiation force on the first mirror attributable to emission of light of a certain central wavelength with sufficient power results in a resonance wavelength band of the cavity shifting between a first state in which a resonance wavelength band of the cavity includes a set of wavelengths shorter than a wavelength band matched to a certain central wavelength, a second state in which a resonance wavelength band of the emitted light is matched to a the certain central wavelength, and the third state in which the resonance wavelength band of the cavity includes a set of wavelengths longer than a wavelength band matched to the certain central wavelength.

A17. The optomechanical device of A1, wherein the optomechanical device is configured so that the first mirror and the second mirror are provided in a common plane.

A18. The optomechanical device of A1, wherein the optomechanical device includes an in-plane device structure.

A19. The optomechanical device of A1, wherein the optomechanical device is configured as an eyewear apparatus.

A20. The optomechanical device of A1, wherein the optomechanical device is configured as an eyewear apparatus, the eyewear apparatus having an eyewear apparatus frame that supports the cavity. B1. An optomechanical device comprising: a light source; a first mirror; and a second mirror forming with the first mirror a cavity; wherein the first mirror is a movable mirror; wherein the optomechanical device is adapted so that the first mirror is moveable responsively to radiation force; wherein the light source emits light at a certain central wavelength, and wherein the optomechanical device is operative so that light emitted from the light source incident on the cavity in a forward direction results in a first set of radiation forces being imparted on the first mirror, and wherein the optomechanical device is further operative so that reflected light having the certain central wavelength incident on the cavity in a backward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction.

C1. An optomechanical device comprising: a light source; a first mirror; and a second mirror forming with the first mirror a cavity; wherein the first mirror is a movable mirror; wherein the optomechanical device is adapted so that the first mirror is moveable responsively to radiation force; wherein the light source emits light at a certain central wavelength, and wherein the optomechanical device is operative so that light emitted from the light source incident on the cavity in a forward direction results in a first set of radiation forces being imparted on the first mirror, and wherein the optomechanical device is further operative so that reflected light having the certain central wavelength incident on the cavity in a backward direction simultaneously with light from the light source being incident on the cavity in the forward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction simultaneously with light from the light source being incident on the cavity in the forward direction, wherein the certain central wavelength is matched to the first resonance wavelength band but not matched to the second resonance wavelength band so that the reflected light at the certain central wavelength is not transmitted by the cavity.

D1. An optomechanical device comprising: a first mirror; and a second mirror forming with the first mirror a cavity; wherein the first mirror is a movable mirror; wherein the optomechanical device is adapted so that the first mirror is moveable responsively to radiation force; wherein during an initial state a resonance wavelength band of the cavity is matched to a certain central wavelength so that the cavity is capable of transmitting light emitted from a light source that emits light at the certain central wavelength, and wherein the optomechanical device is adapted so that a set of radiation forces on the first mirror attributable to emission of light at the certain central wavelength with sufficient power results in a resonance wavelength band of the cavity shifting from a wavelength band at which the resonance wavelength band of the cavity is matched to the certain central wavelength to a wavelength band at which the resonance wavelength band is not matched to the certain central wavelength.

E1. An optomechanical device comprising: a first mirror; and a second mirror forming with the first mirror a cavity; wherein the first mirror is a movable mirror; wherein the optomechanical device is adapted so that the first mirror is moveable responsively to radiation force; wherein during an initial state a resonance wavelength band of the cavity is not matched to a certain central wavelength so that in an initial state the cavity is restricted from transmitting light emitted from a light source that emits light at the certain central wavelength, and wherein the optomechanical device is adapted so that a set of radiation forces on the first mirror attributable to emission of light at the certain central wavelength with sufficient power results in a resonance wavelength band of the cavity shifting from a wavelength band at which the resonance wavelength band of the cavity is not matched to the certain central wavelength to a wavelength band at which the resonance wavelength band of the cavity is matched to the certain central wavelength.

F1. A method comprising: providing an optomechanical device, the optomechanical device being adapted so that forward incident light results in a first set of radiation forces being imparted to optomechanical device, the optomechanical device further being adapted so that backward incident light results in a second set of radiation forces being imparted to the optomechanical device, the optomechanical device having a first transmittivity band when the first set of forces are imparted to the optomechanical device, the optomechanical device having a second transmittivity band when the second set of forces are imparted to the optomechanical device; and directing light toward the optomechanical device at a central wavelength matching the first transmittivity band.

F2. The method of F1, wherein the providing step includes the step of providing a cavity.

F3. The method of F1, wherein the providing step includes the step of providing a cavity having a moveable mirror.

F4. The method of F3, wherein the providing step further includes providing a stop for stopping the moveable mirror at a certain position for stabilization of a current transmittivity band of the optomechanical device.

F5. The method of F1, wherein the method further includes the step of blocking reflected light transmitted by the optomechanical device utilizing the optomechanical device.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than or greater than the mentioned certain number of elements. Also, while a number of particular embodiments have been described, it will be understood that features and aspects that have been described with reference to each particular embodiment can be used with each remaining particularly described embodiment.

We claim:

1. An optomechanical device comprising:
a first mirror; and
a second mirror forming with the first mirror a cavity;
wherein the first mirror is a movable mirror;
wherein the optomechanical device is adapted so that the first mirror is moveable responsively to radiation force;
wherein the optomechanical device includes a mechanical stop for stopping the first mirror at a certain position to result in a certain resonance wavelength band of the cavity being defined; and
wherein the optomechanical device is operative so that light incident on the cavity in a forward direction results in a first set of radiation forces on the first mirror, and wherein the optomechanical device is further operative so that reflected light transmitted through the cavity incident on the cavity in a backward direction results in a second set of radiation forces on the first mirror, a sum of the second set of radiation forces being different from a sum of the first set of radiation forces.

2. The optomechanical device of claim 1, wherein the first mirror is made moveable with use of mechanical suspensions.

3. The optomechanical device of claim 2, wherein the mechanical suspensions are provided by cantilevers.

4. The optomechanical device of claim 1, wherein the second mirror is a stationary mirror.

5. The optomechanical device of claim 1, wherein the first mirror includes a photonic crystal.

6. The optomechanical device of claim 1, wherein the first mirror includes a photonic crystal and wherein the second mirror includes a photonic crystal.

7. The optomechanical device of claim 1, wherein the optomechanical device includes an in-plane device structure.

8. The optomechanical device of claim 1, wherein the optomechanical device is configured so that the first mirror and the second mirror are provided in a common plane.

9. The optomechanical device of claim 8, wherein the first mirror and the second mirror have respective planar structures that extend in a common plane.

10. The optomechanical device of claim 8, wherein the first mirror and the second mirror extend in a common plane.

11. The optomechanical device of claim 8, wherein the first mirror and the second mirror are disposed side by side and extend in a common plane.

12. The optomechanical device of claim 8, wherein the optomechanical device defines a cavity provided as an in-plane optomechanical device having an in-plane device structure.

13. The optomechanical device of claim 1, wherein the mechanical stop is spaced apart from the first mirror.

14. The optomechanical device of claim 1, wherein the mechanical stop is adapted for stopping movement of the first mirror in one direction.

15. The optomechanical device of claim 1, wherein the mechanical stop is adapted to stop movement of the first mirror in a first direction, and wherein the optomechanical device is adapted so that the first mirror is free to move in a second direction opposite the first direction without being stopped by a mechanical stop.

16. The optomechanical device of claim 1, wherein during an initial state a resonance wavelength band of the cavity is not matched to a certain central wavelength so that in an initial state the cavity is restricted from transmitting light emitted from a light source at the certain central wavelength, and wherein the optomechanical device is adapted so that a set of radiation forces on the first mirror attributable to emission of light at the certain central wavelength with sufficient power results in a resonance wavelength band of the cavity shifting from a wavelength band at which the resonance wavelength band of the cavity is not matched to the certain central wavelength to a wavelength band at which the resonance wavelength band of the cavity is matched to the certain central wavelength.

17. The optomechanical device of claim 1, wherein the mechanical stop is provided to include a damped response.

18. The optomechanical device of claim 1, wherein the mechanical stop is provided to include a damped response without oscillation.

19. The optomechanical device of claim 1, wherein the mechanical stop is resistant to adhering with externally disposed objects.

20. The optomechanical device of claim 1, wherein the mechanical stop includes a polymer coating so that the mechanical stop is resistant to adhering with externally disposed objects.

21. The optomechanical device of claim 1, wherein the optomechanical device includes a light source emitting light at a certain central wavelength and wherein the certain position is a position for stabilization of the resonance wavelength band at a wavelength band at which it is matched to the certain central wavelength.

22. The optomechanical device of claim 1, wherein the optomechanical device includes a light source emitting light at a certain central wavelength and wherein the certain position is a position for stabilization of the resonance wavelength band at a wavelength band at which it is matched to the certain central wavelength so that forward directed light emitted by the light source and incident on the cavity is transmitted through the cavity.

23. The optomechanical device of claim 1, wherein the optomechanical device includes a light source that emits light at a certain central wavelength, and wherein the optomechanical device is operative so that light emitted from the light source incident on the cavity in a forward direction results in the first set of radiation forces being imparted on the first mirror, and wherein the optomechanical device is further operative so that reflected light transmitted through the cavity having the certain central wavelength incident on the cavity in a backward direction results in the second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction.

24. The optomechanical device of claim 1, wherein the optomechanical device includes a light source that emits light at a certain central wavelength, and wherein the optomechanical device is operative so that light emitted from the light source incident on the cavity in a forward direction results in the first set of radiation forces being imparted on the first mirror, and wherein the optomechanical device is further operative so that reflected light transmitted through the cavity having the certain central wavelength incident on the cavity in a backward direction results in a the second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction, wherein the certain central wavelength is matched to the first resonance wavelength band but not matched to the second resonance wavelength band so that the reflected light at the certain central wavelength is not transmitted by the cavity.

25. The optomechanical device of claim 1, wherein the optomechanical device includes a light source that emits light at a certain central wavelength, and wherein the optomechanical device is operative so that light emitted from the light source incident on the cavity in a forward direction results in the first set of radiation forces being imparted on the first mirror, and wherein the optomechanical device is further operative so that reflected light transmitted through the cavity having the certain central wavelength incident on the cavity in a backward direction simultaneously with light from the light source being incident on the cavity in the forward direction results in the second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction simultaneously with light from the light source being incident on the cavity in the forward direction, wherein the certain central wavelength is matched to the first resonance wavelength band but not matched to the second resonance wavelength band so that the reflected light at the certain central wavelength is not transmitted by the cavity.

26. The optomechanical device of claim 1, wherein during an initial state a resonance wavelength band of the cavity is matched to a certain central wavelength so that the cavity is capable of transmitting light emitted from a light source at the certain central wavelength, and wherein the optomechanical device is adapted so that a set of radiation forces on the first mirror attributable to emission of light at the certain central wavelength with sufficient power results in a resonance wavelength band of the cavity shifting from a wavelength band at which the resonance wavelength band of the cavity is matched to the certain central wavelength to a wavelength band at which the resonance wavelength band is not matched to the certain central wavelength.

27. The optomechanical device of claim 16, wherein the optomechanical device includes the mechanical stop for stopping the first mirror at a certain position for stabilization of the resonance wavelength band at a wavelength band at which it is matched to the certain central wavelength when light having the certain central wavelength of sufficient power is incident on the cavity.

28. The optomechanical device of claim 1, wherein the optomechanical device is adapted so that radiation force on the first mirror attributable to emission of light of a certain central wavelength with sufficient power results in a resonance wavelength band of the cavity shifting between a first state in which a resonance wavelength band of the cavity includes a set of wavelengths shorter than a wavelength band matched to a certain central wavelength, a second state in which a resonance wavelength band of the cavity is matched to a the certain central wavelength, and a third state in which the resonance wavelength band of the cavity includes a set of wavelengths longer than a wavelength band matched to the certain central wavelength.

29. The optomechanical device of claim 1, wherein the first mirror is provided by a drop ring.

30. The optomechanical device of claim 1, comprising a waveguide optically coupled to a set of edges of the first mirror and the second mirror.

31. The optomechanical device of claim 1, wherein the optomechanical device configured so that the first mirror and the second mirror are provided in a common plane, and wherein the optomechanical device includes a waveguide optically coupled to a set of edges of the first mirror and the second mirror.

32. The optomechanical device of claim 1, comprising a first waveguide optically coupled to a first set of edges of the first mirror and the second mirror and a second waveguide optically coupled to a second set of edges of the first mirror and the second mirror.

33. The optomechanical device of claim 1, wherein the optomechanical device is fabricated in a solid state material system.

34. The optomechanical device of claim 1, wherein the optomechanical device is configured as an eyewear apparatus.

35. The optomechanical device of claim 1, wherein the optomechanical device is configured as an eyewear apparatus, the eyewear apparatus having an eyewear apparatus frame that supports the cavity.

36. An optomechanical device comprising:
a light source;
a first mirror; and
a second mirror forming with the first mirror a cavity;
wherein the first mirror is a movable mirror;
wherein the optomechanical device is adapted so that the first mirror is moveable responsively to radiation force;
wherein the light source emits light at a certain central wavelength, and
wherein the optomechanical device is operative so that light emitted from the light source incident on the cavity in a forward direction results in a first set of radiation forces being imparted on the first mirror, and wherein the optomechanical device is further operative so that reflected light transmitted through the cavity having the certain central wavelength incident on the cavity in a backward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction.

37. The optomechanical device of claim 36, wherein the optomechanical device includes a mechanical stop for stopping movement of the first mirror in a first direction, wherein the optomechanical device is configured so that the first mirror and the second mirror are provided in a common plane, and wherein the optomechanical device includes a waveguide optically coupled to a set of edges of the first mirror and the second mirror.

38. An optomechanical device comprising:
a light source;
a first mirror; and
a second mirror forming with the first mirror a cavity
wherein the first mirror is a movable mirror; wherein the optomechanical device is adapted so that the first mirror is moveable responsively to radiation force;
wherein the light source emits light at a certain central wavelength, and wherein the optomechanical device is operative so that light emitted from the light source incident on the cavity in a forward direction results in a first set of radiation forces being imparted on the first mirror, and
wherein the optomechanical device is further operative so that reflected light transmitted through the cavity having the certain central wavelength incident on the cavity in a backward direction simultaneously with light from the light source being incident on the cavity in the forward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for light incident on the cavity in the backward direction simultaneously with light from the light source being incident on the cavity in the forward direction, wherein the certain central wavelength is matched to the first resonance wavelength band but not matched to the second resonance wavelength band so that the reflected light at the certain central wavelength is not transmitted by the cavity.

39. An optomechanical device comprising:

a first mirror; and a second mirror forming with the first mirror a cavity;

wherein the first mirror is a movable mirror;

wherein the optomechanical device is adapted so that the first mirror is moveable responsively to radiation force;

wherein the optomechanical device includes a light source that emits light at a certain central wavelength, and wherein the optomechanical device is operative so that light emitted from the light source incident on the cavity in a forward direction results in a first set of radiation forces being imparted on the first mirror, and wherein the optomechanical device is further operative so that reflected light having the certain central wavelength incident on the cavity in a backward direction simultaneously with light from the light source being incident on the cavity in the forward direction results in a second set of radiation forces being imparted on the first mirror, wherein a sum of the first set of radiation forces, and a sum of the second set of radiation forces are not equal so that there is defined for the cavity a first resonance wavelength band for light incident on the cavity in the forward direction and a second resonance wavelength band for reflected light transmitted through the cavity incident on the cavity in the backward direction simultaneously with light from the light source being incident on the cavity in the forward direction, wherein the certain central wavelength is matched to the first resonance wavelength band but not matched to the second resonance wavelength band so that the reflected light at the certain central wavelength is not transmitted by the cavity.

40. The optomechanical device of claim 39, wherein the optomechanical device includes a mechanical stop for stopping the first mirror at a certain position to result in the first resonance wavelength band of the cavity being defined.

* * * * *